(12) United States Patent
Groenendijk et al.

(10) Patent No.: US 9,084,804 B2
(45) Date of Patent: Jul. 21, 2015

(54) NON-MEDICAL INCREASE OR MAINTENANCE OF BODY WEIGHT OF A MAMMAL

(75) Inventors: Martine Groenendijk, Barendrecht (NL); Patrick Joseph Gerardus Hendrikus Kamphuis, Utrecht (NL); Mattheus Cornelis De Wilde, Elst (NL); Robert Johan Joseph Hageman, Wageningen (NL)

(73) Assignee: N.V. Nutricia (NL)

( * ) Notice: Subject to any disclaimer, the term of this patent is extended or adjusted under 35 U.S.C. 154(b) by 0 days.

(21) Appl. No.: 13/977,162

(22) PCT Filed: Aug. 11, 2011

(86) PCT No.: PCT/NL2011/050555
§ 371 (c)(1),
(2), (4) Date: Aug. 20, 2013

(87) PCT Pub. No.: WO2012/091548
PCT Pub. Date: Jul. 5, 2012

(65) Prior Publication Data
US 2013/0330424 A1 Dec. 12, 2013

(30) Foreign Application Priority Data
Dec. 28, 2010 (WO) ............... PCT/NL2010/050892

(51) Int. Cl.
| | |
|---|---|
| *A61K 31/70* | (2006.01) |
| *A01N 43/04* | (2006.01) |
| *A61K 31/675* | (2006.01) |
| *A23L 1/29* | (2006.01) |
| *A23L 1/30* | (2006.01) |
| *A23L 1/302* | (2006.01) |
| *A61K 31/14* | (2006.01) |
| *A61K 31/202* | (2006.01) |
| *A61K 31/355* | (2006.01) |
| *A61K 31/375* | (2006.01) |
| *A61K 31/4415* | (2006.01) |
| *A61K 31/519* | (2006.01) |
| *A61K 31/683* | (2006.01) |
| *A61K 31/685* | (2006.01) |
| *A61K 31/7072* | (2006.01) |
| *A61K 31/714* | (2006.01) |
| *A61K 33/04* | (2006.01) |
| *A61K 45/06* | (2006.01) |
| *A61K 31/20* | (2006.01) |
| *A61K 31/661* | (2006.01) |
| *A61K 31/7056* | (2006.01) |

(52) U.S. Cl.
CPC ............ *A61K 31/675* (2013.01); *A23L 1/296* (2013.01); *A23L 1/302* (2013.01); *A23L 1/3008* (2013.01); *A23L 1/3012* (2013.01); *A61K 31/14* (2013.01); *A61K 31/20* (2013.01); *A61K 31/202* (2013.01); *A61K 31/355* (2013.01); *A61K 31/375* (2013.01); *A61K 31/4415* (2013.01); *A61K 31/519* (2013.01); *A61K 31/661* (2013.01); *A61K 31/683* (2013.01); *A61K 31/685* (2013.01); *A61K 31/7056* (2013.01); *A61K 31/7072* (2013.01); *A61K 31/714* (2013.01); *A61K 33/04* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2003/0124237 A1* | 7/2003 | Kuhlman et al. ............. | 426/580 |
| 2007/0254062 A1 | 11/2007 | Singhal et al. | |
| 2010/0104545 A1 | 4/2010 | Rosales et al. | |

FOREIGN PATENT DOCUMENTS

| | | | | |
|---|---|---|---|---|
| EP | 0302807 | A2 | 2/1989 | |
| JP | S64-63358 | A | 3/1989 | |
| JP | 2005-514017 | A | 5/2005 | |
| JP | 2007-068541 | A | 3/2007 | |
| JP | 2010-531351 | A | 9/2010 | |
| WO | 02/088159 | A1 | 11/2002 | |
| WO | 03055322 | A1 | 7/2003 | |
| WO | 2004/026294 | A1 | 4/2004 | |
| WO | 2005/060952 | A1 | 7/2005 | |
| WO | 2007/073178 | A2 | 6/2007 | |
| WO | 2009/002146 | A1 | 12/2008 | |
| WO | 2009002166 | A1 | 12/2008 | |
| WO | WO 2009/002146 | A1 * | 12/2008 | ............. A61K 31/20 |
| WO | 2010/002257 | A1 | 1/2010 | |

OTHER PUBLICATIONS

Hashioka et al. Free Radical biology & Medicine (2007), vol. 42, pp. 945-954.*
Wurtman Metabolism (2008), vol. 57 (Suppl 2), S6-10, pp. 1-7.*
Holmes-McNary et al. Am. J. Clin. Nutr. (1996), vol. 64, pp. 572-576.*

(Continued)

*Primary Examiner* — Patrick Lewis
(74) *Attorney, Agent, or Firm* — Banner & Witcoff, Ltd.

(57) ABSTRACT

Non-medical use of at least two components selected from the group of: (i) nucleoside equivalents, (ii) n-3 polyunsaturated fatty acids selected from the group of DHA, DPA and EPA, (iii) vitamins B, (iv) phospholipids, (v) antioxidants and (vi) cholines—with the proviso that at least one (i) nucleoside or at least one (iii) vitamin B is present—for increasing or maintaining the body weight, for improving the ability to perform an activity of daily living of a mammal, for maintaining the ability to perform an activity of daily living of a mammal, or for reducing a deterioration in the ability to perform an activity of daily living of a mammal.

34 Claims, No Drawings

(56) References Cited

OTHER PUBLICATIONS

Binder, Ellen F. et al. The Relation Between Psychometric Test Performance and Physical Performance in Older Adults. 1999 J. Gerontol 54, M428-432.

Borsheim, Elisabet et al. Effect of amino acid supplementation on muscle mass, strength and physical function in elderly. 2008 Clin Nutr. 27, 189-195.

Campion, Edward W. Aging Better. 1998 N Engl J. Med 338(15) 1064-66.

Chin A Paw, Marijke J. M. et al. How to Select a Frail Elderly Population? A Comparison of Three Working Definitions. 1999 J Clin Epidemiol 52(11) 1015-1021.

Chin A Paw Marijke J. M. et al. Inactivity and Wright Loss: Effective Criteria to identify Frailty. 2003 J Nutr Health Aging 7(1) 55-60.

Delcourt, Cecile et al. Smoking and Age-related Macular Degeneration. 1998 Arch Ophthalmology 116, 1031.

Dubois, Bruno et al. Revising the definition of Alzheimer's disease: a new lexicon. 2010 Lancet Neurol 9 1118-1127.

Evans, William J. et al. Nutrition, exercise, and healthy aging. 1997 J American Dietetic Association 97(6), 632.

Faber, Marjan J. et al. Effects of Exercise Programs on Falls and Mobility in Frail and Pre-Frail Older Adults: A Multicenter Randomized Controlled Trial. 2006 Arch Phys Med Rehabil 87 885-96.

Faulkner, John A. et al. Age-related changes in the structure and function of skeletal muscles. 2007 Proc Au P S 38; 69-75.

Ferrucci, Luigi et al. Progressive versus Catastrophic Disability: A Longitudinal View of the Disablement Process. 1996 J. Gerontol Med Sci 51AM123-M130.

Folstein, Marshal F. et al. Mini-Mental State, A Practical Method for Grading the Cognitive State of Patients for the clinician. 1975 J Psychiatr Res 12:189-98.

Graham, James E. et al. Frailty and 10-Year Mortality in Community-Living Mexican American Older Adults. 2009 Gerontol 55 644-651.

Goggins, William B. et al. Frailty Index as a Measure of Biological Age in a Chinese Population 2005 60 1046.

Guerin, Olivier et al. Different modes of weight loss in Alzheimer disease: a prospective study of 395 patients1-3. 2005 Am J Clin Nutr 82(2) 435-441.

Hansson, Oskar et al. Association between CSF biomarkers and incipient Alzheimer's disease in patients with mild cognitive impairment: a follow-up study. 2006 Lancet Neurol 5:228-234.

Holmes, Susan. Nutrition and eating difficulties in hospitalised adults. 2008 Nursing standard, 22(26) 47-57.

Jones, David M. et al. Operationalizing a Frailty Index from a Standardized Comprehensive Geriatric Assessment. 2004 J Am Geriatr Soc 52 1929-33.

Milne, AC et al. Protein and energy supplementation in elderly people at risk from malnutrition (Review). 2009 Cochrane review.

Muller, Erich A. Influence of Training and of Inactivity on Muscle Strength. 1970 Arch Phys Med Rehabil 51 449-462.

Pijnappels, Mirjam et al. Identification of elderly fallers by muscle strength measures. 2008 Eur J Appl Physiol. 102 (5): 585-592.

Pratico, Domenico et al. Increase of Brain Oxidative Stress in Mild Cognitive Impairment. 2002 Arch Neurol 59:972-976.

Roberts, E. Robert. Reliability of the CES-D Scale in Different Ethnic Contexts. 1980 Psychiatr Res 2 125-134.

Schuurmans, Hanneke et al. Old or Frail: What Tells Us More? 2004 J Gerontol Biol Sci Med Sci 59 M962-5.

Skelton, Dawn A. et al. Strength, Power and Related Functional Ability of Healthy People Aged 65-89 Years. 1994 Age and Aging 23, 371-377.

Studenski, Stephanie et al. Clinical Global Impression of Change in Physical Frailty: Development of a Measure Based on Clinical Judgment. 2004 J Am Geriatr Soc 52 1560-6.

Theou, Olga et al. An exploration of the association between frailty and muscle fatigue. 2008 Appl Physiol.

Washburn, Richard A. et al. The Physical Activity Scale for the Elderly (PASE): Evidence for Validity. 1999 J Clin Epidemiol 52, 643-651.

Office Action issued for corresponding European Patent Application No. 11817429.1, dated Mar. 7, 2015.

Office Action issued for corresponding Australian Patent Application No. 2011353204, dated Apr. 24, 2015.

Office Action issued for corresponding Australian Patent Application No. 2011353251, dated Apr. 29, 2015.

Office Action issued for corresponding Japanese Patent Application No. 2013-547376, dated May 19, 2015.

Scheltens et al.; "Efficacy of a medical food in mild Alzheimer's disease: A randomized, controlled trial"; Elsevier, Alzheimer's & Dementia 6, 2010, 1-0.

* cited by examiner

NON-MEDICAL INCREASE OR MAINTENANCE OF BODY WEIGHT OF A MAMMAL

RELATED APPLICATION DATA

This application is a National Stage Application under 35 U.S.C. 371 of co-pending PCT application PCT/NL2011/050555 designating the United States and filed Aug. 11, 2011; which claims the benefit of PCT patent application PCT/NL2010/050892 and filed Dec. 28, 2010 each of which are hereby incorporated by reference in their entireties.

FIELD OF THE INVENTION

The invention relates to a combination of specific components for use in increasing or maintaining body weight. The invention also relates to a nutritional composition that is particularly suitable for such use.

The invention also relates to the specific relevant benefits that can be achieved in such persons, like improvement of stamina, an increased degree of activity during daytime and associated change in lifestyle.

BACKGROUND OF THE INVENTION

Body weight of humans is determined by the weight of the different parts in the body, like that of bones, muscle, organs, vessels, adipose tissue, et cetera. During lifetime the contributions of each body part to the total body weight changes. After maturation of the human body has stopped, typically muscle mass will gradually and steadily decrease with time. This decrease results in a decrease of lean body mass (LBM, which is the body mass minus the mass of adipose tissue), despite the fact that total body mass (or body weight) may increase, e.g. due to an increase of the mass of adipose tissue and changed masses of other parts of the body. Ferruci et al. reported about the progression of loss of muscle strength during aging (Ferruci et al. (1996) J Gerontol Med Sci, 51AM123-M130). The strength of a muscle is considered to be dependent on its mass. Its mass depends on the number of muscle fibres, which decreases only after 55 years of age to about 50% at the age of about 80 years, their length, which depends on their trophic condition, and the cross-sectional area, which depends on training (Faulkner et al. (2007) Proc Au P S, 38; 69-75). Muscle strength (strength of handgrip or quadriceps) in normal persons appeared to decrease about 0.5% per year after the $30^{th}$ year. Typically, this rate of decline of muscle strength increases with age. After the $65^{th}$ year of age, this decrease in muscle strength has reached a magnitude of 1.5% per year for arm muscles and about 3.5% for leg muscle (Skelton et al (1994) Age and Aging, 23, 371-377). Similar age-associated changes in body composition and muscle strength have also been described by Evans, Cyr-Campbell (1997), J American Dietetic Association, 97(6), 632, and by Campion (1998) N Engl J med, 338(15), 1064-66.

It is important to note that, apart from these chronic age-associated decreases in muscle mass and lean body weight, also temporal and mostly reversible changes therein can occur, which in most cases depend on the applied exercise efforts. For example, Muller observed that during long term bed rest, muscle strength decreased at a rate of about 1% per day (Muller (1970) Arch Phys Med Rehabil, 51, 449-462).

These losses in body weight, lean body weight, muscle mass and muscle strength during aging are considered to be normal and physiological, though undesirable. It would be desirable to provide a way to slow down such effect of normal aging, or even reverse the loss.

It should be noted that in part of the human population these losses have occurred at a greater speed or have occurred for a longer period of time to reach a critical level. This abnormally large weight loss is in most cases associated with several health problems which occur at the same time. It is thought that a complex general and non-specific malfunction of the human body causes a low capability of the human body to adapt to the prevalent circumstances to which the individual is exposed. This general condition is recognized by physicians as an independent health problem for which the word sarcopenia was proposed. In the past, different tools have been used to arrive at the diagnosis sarcopenia. Further, abnormal weight loss may result in health problems, in particular frailty (mild or moderate) or prefrailty.

Frailty is a large problem to the individual which experiences it, to the environment and to society. It has a large impact on the individual's life and creates huge costs for medical care. For this reason, the problem is recognized in the prior art as a geriatric syndrome that is distinct from disability and comorbidity. In addition, a relatively low lean body mass and body weight in elderly and especially in persons experiencing neurological problems, is common and a large problem, which has not yet been solved in the prior art.

Food intake, lifestyle and metabolic properties, including energy expenditure, of an individual change with increasing age, which may lead to what has been called a "physiologic anorexia of aging". Dietary habits, nutrient intake, life style and the aging process are interrelated. For example, with decreasing activity during the applied life style, and the age-associated decline in basal metabolic rate, neuro-endocrine function, immune function and taste and smell perception, older people tend to consume less food, and consequently fewer nutrients, which may lead to a nutritional status, which does not the specific requirements of the elderly of the frail individuals. This complex combination of events which is specific to aging individuals, can result in a further decrease in body weight, lean body mass or body mass index (BMI). This may even result in frailty, as defined above. whereas, the use of specific components to reduce loss in body weight or increase body weight in order to prophylactically or therapeutically treat frailty is generally considered as a medical treatment, the present disclosure is in particular directed at a non-medical use. Involuntary weight loss during aging above 65 years is strongly associated with impaired mood and low stamina.

In a specific embodiment of the invention, the specific combination of components according to the invention was found not only to increase BMI, but also resulted in an improvement of the activities of daily living (ADL). Further it may improve the cognitive function. The composition according to the invention may also have a beneficial effect on exhaustion or fatigue, as will be explained below.

The combination of low stamina, low drive to perform normal activities to keep independence and low abilities of skeletal muscles to allow the activities of daily living may result in a low degree of activity during daily life, including the ability to purchase, prepare or consume adequate food quality and quantity.

Therefore, there is a need to effectively improve the nutritional status in mammals, ion particular humans, more in particular in elderly, having an undersirably low body weight (low BMI in humans), in particular by increasing lean body mass, healthy body weight, muscle capacity. Preferably, these effects are achieved in non-frail or prefrail persons, frail or prefrail elderly or elderly having a BMI below 23.5 kg/m².

More preferably, these improvements in health result in a higher amount of activities during daytime, especially during wake time and in general a better functioning in life and quality of life.

This specific improvement of the nutritional status of a subject is, in particular a non-frail or prefail human having a relatively low body weight, is defined to be the nutritional management of the (nonfrail or prefrail) consumer. In the nutritional management of consumers, and especially elderly it is also important to recognize the problem of xerostomia or a dry mouth in general or during eating, and the problem of hypochlorhydria, i.e. the reduced secretion of hydrochloric acid by the stomach, in general or after food intake or after smelling or seeing the food. In one embodiment of the invention it is an objective to provide a nutritional composition which, when consumed, is well tolerated and even appreciated by persons who suffer from xerostomia or hypochlorhydria.

It is known in the prior art that supplementation of protein and energy to elderly who are at risk from malnutrition produces a small but consistent weight gain (Milne et al. (2009) Cochrane review). Healthy persons like athletes can increase their BMI, when very high amounts of specific proteins, peptides or amino acids are consumed, in particular when this is combined with an exercise protocol. The known approach to supplement additional protein and energy demands consumption of food on top of daily meals, and a proper organ function, for dealing with the large amount of dietetic protein (i.e. nitrogen). in particular, the elderly, may experience difficulties with consuming large quantities or volumes of food, may suffer from impairments in body and organ function or from early satiety and low appetite, have practical problems with cooking and with consuming the food products, and are not keen on or capable of applying exercise programs (Holmes (2008) Nursing standard, 22 (26), 47-57).

Accordingly, there is a need for an alternative way of nutritional management of elderly which are in need of an increased body weight, body mass index, lean body weight, muscle mass or muscle strength, to perform appropriately, especially elderly Preferably, the composition according the invention achieves all benefits as described above at about the same time. This is observed in elderly in general (above 65 years of age), but also in a subgroup thereof, the oldest one (persons above 75 years of age). In a preferred embodiment, the nutritional composition according to the invention is to be used for treating increasing low body weight or BMI and for improving activities of daily living (ADL), especially in persons older than 50 years of age, more in particular those older than 65 years of age (elderly) and in particular older than 75 years of age (the oldest). The composition according to the invention may also be used to combat other undesirable effectsy, such as exhaustion or fatigue by its effect on muscle power, and thrive or stamina and the effect on neurological performance, in particular cognition.

BACKGROUND PRIOR ART

In WO2009/002146 (NV Nutricia), a composition is disclosed which comprises DHA or EPA, in combination with uridine or its equivalent and optionally a range of other components to support activities of daily living. The composition can be administered to elderly and locomotor function appeared improved by administering these components. Also, protein could be included in the composition of the invention, in order to improve muscle strength, when administered to frail elderly. In order to achieve this, in particular 1 to 5 g protein per 100 ml of a liquid composition was included, wherein the protein comprises more than 80 weight % milk-derived proteins.

WO2010/002257 (NV Nutricia) discloses the use of a nutritional preparation comprising more than 18 energy percent protein (preferably 22 to 32 en %), whey protein, at least 12 g leucine per 100 g proteinaceous matter and a lipid fraction which comprises at least one of EPA, (n-3)DPA, DHA and (n-3) ETA for improving muscle function in a mammal. The improvement of the function of muscle was in terms of maximum force, maximum contraction velocity and maximum relaxation velocity, all corrected for muscle mass. This improvement was claimed to occur when the mammal suffered from specific diseases, in particular cancer or during "aging" and was claimed to result in improving daily activity, physical performance and quality of life. Frail individuals as such were not mentioned and neither were elderly with a low BMI or elderly being frail. The composition as disclosed comprises preferably the components as mentioned and in addition specific indigestible oligosaccharides, glutamine, cysteine, oligosaccharides, carnitine and taurine. Though soy protein and wheat protein were mentioned the inclusion of casein instead of these vegetable proteins was preferred. Nucleotides and uridine sources were not mentioned.

WO 2005/060952 (NV Nutricia) relates to a composition comprising in a daily dosage form 14 to 1000 mg panthothenic acid (vitamin B5) for stimulating appetite, whereby body weight and muscle mass is increased in specific groups of diseased humans. This was surprising, since panthothenic acid had been reported before as a hunger suppressant. The composition may further comprise folic acid, vitamin C (as antioxidant), and vitamin B6 and B12 as part of a common vitamin premix.

WO2007/073178 (NV Nutricia) discloses a drink liquid for Alzheimer patients (Example 3) comprising a nucleoside equivalent (UMP), fish oil comprising DHA and EPA, vitamin B6, folic acid and vitamin B12, phospholipids, vitamin C (as antioxidant), and choline. The claimed effect is not disclosed.

WO2004/026294 (Nestec S.A.) discloses a nutritional composition which comprises leucine and at least one of isoleucine, lysine, methionine, phenylalanine, threonine, tryptophan, valine or histidine in free or salt form, wherein free leucine is present in an amount of 10 to 35 weight % of the total amount of amino acids. Such composition was claimed to be useful for controlling tumour-induced weight loss, for stimulating protein synthesis, ameliorating loss of muscle in a human or for the dietary management of malnutrition.

SUMMARY DESCRIPTION OF THE INVENTION

It has now been found that lean body mass (LBW) or the body mass index (BMI) can be increased in mammals, or by providing a nutritional or pharmaceutical composition comprising a specific combination of active components. Further, it has been found that LBW or BMI can be increased for non-medical purposes.

Accordingly, the invention relates to the non-medical use of a composition comprising at least two, preferably three, and more preferably four components (as active ingredients) selected from the group of (i) nucleoside equivalents, (ii) n-3 polyunsaturated fatty acids selected from the group of DHA, DPA and EPA, (iii) vitamins B selected from the group of vitamin B6, vitamin B9 and vitamin B12, (iv) a phospholipid, (v) an antioxidant selected from the group of vitamin C, vitamin E and selenium (including selenium compounds), and (vi) cholines—with the proviso that at least one (i) nucleoside or at least one of said (iii) vitamins B is present for increasing or maintaining the body weight of a mammal. This can be accomplished by administering the components used according to the invention, wherein the components are administered to the mammal in a diet without essentially increasing the daily caloric intake of the mammal. The combination is used for increasing or maintaining the body weight for a non-medical reason. Such reason may in particular be cosmetic, such as to improve physical appearance, especially of elderly people, or the use may contribute to improving quality of life for other than for medical reason. E.g. normal aging effects may be slowed down, or it may contribute to letting elderly live independently until a later age. In particular, elderly with an age above 65 years of age, preferably with an age may benefit from a use according to the invention.

Further, the invention relates to the non-medical use of at least two components selected from the group of: (i) nucleoside equivalents, (ii) n-3 polyunsaturated fatty acids selected from the group of DHA, DPA and EPA, (iii) vitamins B selected from the group of vitamin B6, vitamin B9 and vitamin B12, (iv) a phospholipid, (v) an antioxidant selected from the group of vitamin C, vitamin E and selenium (including selenium compounds), and (vi) cholines—with the proviso that at least one (i) nucleoside or at least one of said (iii) vitamins B is present—are used in a non-medical or medical method for improving the ability to perform an activity of daily living of a mammal, for maintaining the ability to perform an activity of daily living (ADL) of a mammal, or for reducing a deterioration in the ability to perform an activity of daily living of a mammal.

When referred herein after to a 'vitamin B', in general a vitamin B selected from the group of folates, pyridoxins and cobalamines is meant, unless specifically stated otherwise. When referred herein after to an 'antioxidant', in general an antioxidant selected from the group of vitamin C (ascorbates), vitamin E (tocopherols) and selenium (including selenium compounds) (v) is meant, unless specifically stated otherwise.

When referring to an acid (e.g. ascorbic acid or folic acid), its conjugated anion, e.g. ascorbate respectively folate, is meant to be included, unless specifically stated otherwise. Likewise, when referring to a base (e.g. folate, ascorbate), its conjugated acid (e.g. folic acid, respectively ascorbic acid) is meant to be included unless specifically stated otherwise.

Further, the invention relates to a nutritional composition comprising (i) at least two components selected from the group of uridine and uridine monophosphate, (ii) DHA and EPA, (iii) a vitamin B, (iv) a phospholipid, v) an antioxidant, and (vi) a choline.

Such composition is in particular suitable for a use according to the invention.

The term 'active ingredient' or 'active component' is used herein in particular for (i) nucleoside equivalents, (ii) n-3 polyunsaturated fatty acids selected from the group of DHA, DPA and EPA, (iii) vitamins B, (iv) phospholipids, (v) antioxidants and (vi) cholines, which are effective in one or more of the claimed uses. They may be present in a combination or composition (for use) according to the invention in any physiologically acceptable form.

If a specific compound falls in more than one of these groups (i)-(vi) of active ingredients it typically provides an active ingredient of both groups. The actual dosage or concentration provided for each group can be determined based on how the compound is used/metabolised after administration. For example, phosphatidyl choline (PC) is both a phospholipid and a choline. As a phospholipid it can be active in the distrubution/emulsification of lipids, and thereafter it can be metabolised to release the choline, which is an essential component for mammals, such as humans. Thus, a composition comprising PC comprises both an active ingredient of the group of phospholipids and of the group of cholines. Another example of a compound providing more than one type of active ingredients is Citicoline (cytidine diphosphate-choline), which provides both choline and a nucleoside source.

In an advantageous embodiment, a nutritional the use of a composition used according the invention results in a further improvement in the amount of activities of daily living that can be performed and an increased muscle mass, muscle strength or muscle function, when also a specific protein amount is included in the composition according to the invention. In particular, the composition according the invention may be used to improve stamina, to increase degree and frequency of feeling more energetic, to decrease duration, severity or frequency of feeling tired or exhausted or feeling fatigue, or to increase eagerness to demonstrate initiatives and become more active. In addition the composition according the invention can improve gait.

It has also been found that mammals physically benefit from treatment with a specific combination of active ingredients such that one or more of body weight, body mass index, or lean body weight are better maintained or even increased without the need to increase the daily caloric intake of said mammals.

The components as described above can be combined with a specific protein composition to obtain a stronger effect on LBM or BMI.

The term "or", as used herein, means also "and", unless specified otherwise or the context dictates otherwise. Hence, "option A or B" means any of the options A, B and A and B.

The term "a" or "an", as used herein, means "at least one" unless specified otherwise.

When referring to a noun (e.g. a compound, an additive etc.) in singular, the plural is meant to be included, unless specified otherwise.

When referring herein to an acid, e.g. a fatty acid or folic acid, this term is meant to include the conjugated bases of said acid (e.g. folate), salts of the acids and derivatives of the acid of which the body is capable of converting it into the acid (e.g. fatty acid esters, such as triglycerides), unless specified otherwise.

When referring herein to dosages, these are in particular intended for adult humans. The skilled person will be able to determine a suitable dosage for other mammals based on common general knowledge, the information disclosed herein and optionally a limited amount of routine testing.

When referring to a mammal, preferably the mammal is a human mammal, more preferably an elderly human mammal.

DETAILED DESCRIPTION OF THE INVENTION

Definition of Frailty

For the purpose of this document, the inventors apply the following definition for frailty, which includes the practical approaches of many scientists (like Fried, Ory, and Chin A Paw). A person is deemed to be frail when the individual's condition in a recent period of time complies with at least 3 of the following list of (6) classes of symptoms (frailty criterions):

1. Muscle weakness,
2. Excessive feelings of exhaustion or fatigue,
3. Abnormally low physical activity,
4. Slow or unsteady gait, 5. Weight loss, and
6. Neurological dysfunction The degree of malfunction of each of the mentioned classes of symptoms can be measured by applying recognized methods that are known in the prior art. For the purpose of this invention, the application of the following methods is preferred:

Criterion 1 (Muscle Weakness)

For determining muscle weakness one of the following list: a) for muscles of the arm: hand grip strength or quadriceps strength, b) for the leg the method as described by BØrsheim et al. (2008) Clin Nutr. 27, 189-195; or as described in Pijnappels et al. (2008) Eur J Appl Physiol. 102(5): 585-592 can be applied. Belonging to the lower 20% of the group of age and gender matched persons resulted in fulfilment of this frailty criterion.

Criterion 2 (Feeling of Exhaustion or Fatigue)

For determining the degree of exhaustion or fatigue, one can assess one or more of a) mental fatigue, b) the perception of exerting a standardized exercise protocol, muscle capacity or muscle power, or c) lung capacity. Preferably, method a) is done by applying a questionnaire as known in the prior art, e.g. the CES-D scale as described by Roberts (1980) Psychiatr Res, 2, 125-134, so scoring on statements like "I cannot get going" or "I feel that everything I do is an effort". This measure is strongly related to the degree of stamina of the individual. Method b) is a measure of physical exhaustion and can for example be done by applying the Borg scale for measuring perceived exertion (Borg (1998) Human kinetics, Champaign, Ill.; Nybo (2003) Med Sci Sports Exerc, 35, 589-594). Method c) is a measure of the capacity of a human being to provide sufficient oxygen (air) to the body. The preferred method for applying it, is measuring forced expiratory volume (FEV1) in one second, which should be below 30% of the normal value, for individuals of similar age and gender, in order to meet the criterion.

Measurement of the degree of physical exhaustion or fatigue, as recommended in method b) can be done in several ways, which all represent ways that reflect the capacity of the neuro-muscular system to exert labour and be active. For example, the amount of physical activities can be measured, by attachment of devices to the person to be tested, and measuring the amount of physical activity which is voluntarily applied normally during wake time. This amount can also be related to the amount of sleep or rest that is needed to recover from it, and be put in a score. Secondly, the capacity of the muscle to maintain a certain force for a certain time is a useful measure. Preferably, this force that needs to be maintained is at 15 to 80% of the maximal force the muscle can provide, in order to reflect better the activities as applied in normal life. Thirdly, the speed with which physical exhaustion is developed can be determined. For example, the amount of power a muscle can exert in a certain period of time can be determined; e.g. by measuring the force multiplied with the distance (in a movement) that the force was exerted, e.g. by swinging a leg at a certain velocity. Equipment for measuring these advanced parameters is commercially available. The speed with which a muscle can become tired, or in other words, the time that a certain force can be maintained, is a valuable measure of the capability of an organism to apply daily activities. When the measured values for these parameters in the tested person belong to the lower 20% of such values for a group of persons of similar age and gender, the person is deemed to comply with this criterion of frailty.

It is important to recognise that larger muscle strength does not in all circumstances necessarily lead to a higher muscle capacity or power or a better endurance. The larger force which is provided by the muscle may have exhausted endogenous energy supplies more, which deteriorates the time or distance that the muscle can exert the force, and therefore does not increase muscle capacity or power. A larger force may also increase negative feedback signals from peripheral joints, muscles and tendons. Muscle capacity or muscle power also better reflects the muscle effort that needs to be done to apply an activity of daily living (Theou et al. (2008) Appl Physiol, Katsiaris, et al, 2005). Therefore, muscle capacity or muscle power, and not muscle strength, provides useful information about the state of exhaustion and fatigue, and especially physical exhaustion and fatigue of a subject. The force that a skeletal muscle can apply also influences the maximal velocity with which a certain movement can be made. A high movement velocity does not automatically result in a large endurance or a good recovery after exercise, which are required for performing a large amount of activities or showing a high mobility during wake time over the day.

Criterion 3 (Physical Activity)

For determining the magnitude of physical activity of a human, one or more methods of the following list can be applied: a) determination of the amount of basic activities as applied during daily life (as described above), and b) determination of the amount of instrumental activities, as applied during daily life. Especially the measurement of instrumental activities is a valuable measure. A reliable method to do this is assessment of the "Physical Activity Scale for the Elderly" (PASE), as described by Washburn et al. (1999) J Clin Epidemiol 52, 643-651; "The physical activity scale for the elderly; evidence for validity". For men, a score of less than 30 and belonging to lowest 20% part fulfilled this criterion for frailty. For women, the threshold value was <27.5 (Graham et al. (2009) Gerontol, 55, 644-651).

Criterion 4 (Gait)

For determining the gait of a human, tests can be applied, like those described in the "Modified Physical Performance Test" (PTT), as disclosed by Binder et al. (1999) J Gerontol, 54, M428-432, like the preferred a) measure of "balance", as e.g. done by determining the way how a frail person is capable of taking a penny from the floor, or b) time and way to walk 5 to 15 meters, or c) time and way to raise from a chair. For example, for method b) the criterion for frailty was fulfilled when the person belonged to 20% of persons with regard to the time needed. The threshold values per gender as mentioned in Graham et al. (2009) Gerontol, 55, 644-651 can suitably be applied.

Criterion 5 (Weight Loss)

For determining the presence of undesired weight loss, it is important to avoid confusion with acute weight loss as caused by a (serious) disease or trauma or an underlying pre-death syndrome. In one embodiment of the invention, frailty as the result of cachexia is excluded from the group of persons wherein the composition according to the invention is effective. In one embodiment of the invention, this exclusion of persons who have become frail because of cachexia is preferred. In this way, frail individuals which comply with the definition as given above differ from the individuals which have developed a frailty that results from these diagnosed conditions, related to acute phases during diseases and briefly before death.

With regard to determining the value of BMI, which should give concerns for becoming "frail", it is important to be aware of the fact that optimal BMI values change with age. While at young and middle age a BMI value between 20 to 25 kg per square meter is considered to be most healthy, at older age, e.g. above 65 years of age and especially above 75 years of age, a BMI below 23.5 is considered to be undesirable (Chin A Paw et al. (2003) J Nutr Health Aging 7(1), 55-60, or Chin (1999) J Clin Epidemiol 52 (11), 1015-1021). The preferred list of diagnostic tools for establishing a too low body weight, lean body mass or muscle mass aims to be suitable for the aged population.

For the purpose of the invention, the inventors feel that it is desirable to look carefully at the metabolic condition of the individual who suffers from a low BMI, body weight or muscle capacity. When such low body weight is the result of an acute process, the metabolic condition of the individual differs on essential points from that of a person who experiences a more generalized metabolic problem. This difference has also been made by others, for example for Alzheimer patients (Guerin et al. (2005) Am J Clin Nutr, 82 (2), 435-441). Part of the Alzheimer patients appear to experience sudden and severe weight loss as a result of intercurrent events, like institutionalization, a major change in life style, a trauma or the presence of a major disease, while a different part suffered from a more chronic weight loss. Therefore it is preferred that the BMI value, as proposed as a limit for meeting one criterion of frailty, is assessed in the absence of an acute phase condition, i.e. the absence of a diagnosed disease selected from a cancer, AIDS, a COPD, an infection, pre-death, pre-death associated with anorexia, surgery, an accident and similar major trauma, or in an alternative embodiment the acute phases during these diseases or conditions. The presence of the acute phase during these diseases can be determined by measuring a biomarker as known in the prior art, e.g. measuring plasma concentrations of acute phase proteins, like tranthyretin, alpha1-acid glycoprotein, C-reactive protein, or measuring concentrations of cytokines which are representative of acute infections or severely progressed disease, like IL-1, IL-6 or TNF-α. It is important to note that a disease, like cancer, chronic obstructive pulmonary diseases, AIDS and other diseases or pre-death, at some stage can cause a frailty condition that is acute and severe. The inventors find that the metabolic condition of such individual is completely different from that of an individual suffering from a frailty that origins from a generalized metabolic inability to cope with the daily stresses from the outside world. Therefore, in the context of this invention, frailty, which is treated and solved by administering the nutritional or pharmaceutical composition according the invention, is not this acute-, and disease- or trauma-related type of advanced weight loss or frailty. Instead, it is the frailty as defined below and caused by a general and complex deterioration of the body to adapt the external stresses, as can have been acquired during life e.g., by applying bad life style including bad dietary habits, exposure to toxicants or as a result of time, as occurs during aging, in particular by aging after 65 years of age and more in particular the frailty as caused by a chronic deterioration of adaptive responses.

Further, a method for determining involuntary weight loss can be used for assessing whether criterion 5 applies, applying the criterion of 4.5 kg undesired weight loss in the previous year, or 5-10% of body weight within 6-12 months or less. Involuntary weight loss of a subject is weight loss occurring despite the subject's aim to maintain or increase its bodyweight (on the subject's own behalf or after advice of career or health care professional). Such weight loss can be determined routinely by comparing present weight at with the weight in a period 1-2 years earlier and asking the subject whether he aimed to maintain or increase his body weight.

Further, a method can be used applying the criterion of 6 kg undesired or unexplainable weight loss during previous 2 years. Such weight loss can be determined routinely by comparing present weight at with the weight in a period 2 years earlier and asking the subject whether he aimed to maintain or increase his body weight and whether he is aware of any other reasons that might explain a weight loss, A pre-death condition can be diagnosed by a physician. Measurement of transthyretin and α1-acid glycoprotein in blood plasma of both genders and the determination of low blood albumin and high C-reactive protein in blood of males, as applied by Carriere (POLA Group) et al. (1998) Arch Ophthalmology, 116, 1031) is recommended for establishing predeath risk.

Criterion 6 (Neurological Dysfunction)

For determining the degree of neurological dysfunction application of the following list is preferred: a) establishment of a tremor or a locomotor dysfunction different from the balance and performance tests applied in measuring gait performance; b) measurement of cognitive function (impairwent); c) determionation of verbal fluency; d) measurement of speed of conductance of electrical signals over nerves; e) analyses of sensory functioning, to establish a problem related to hearing, vision, tasting, smelling and touch); f) measurement of a emotional or psychological condition, like establishing the presence of major depression, an affect disorder or an anxiety disorder; g) determination of incontinence or the daily occurrence of significant involuntary urinary loss, and h) the presence of a major sleep disorder, like chronic insomnia or sleep apnea. Methods to assess neurological dysfunction have been described in the prior art and include the DSM IV methods, and the measurements as described in the corresponding domains in common frailty assessment methods, like the Groningen frailty indicator (Schuurmans et al. (2004) J Gerontol, Biol Sci, Med Sci, 59, M962-5), the comprehensive geriatric assessment (FI-SGA: Goggins et al. (2005) 60, 1046; Jones et al. (2004) J Am Geriatr Soc, 52, 1929-33) or the clinical global impression of change in physical frailty (CGIC-PF: Studenski et al. (2004) J AM Geriatr Soc, 52, 1560-6). Involuntary urine loss is deemed to be significant when it exceeds 10 ml a day.

A subject is considered to meet this neurological dysfunction criterion of frailty when b) is met (cognitive impairment) or, when a combination of at least two of the other criterions has been fulfilled. Cognitive impairment can be assessed by methods known in the prior art, for example by applying measures of the domains related to the measurement of verbal memory, visuospatial memory and attention-executive abilities. Preferred methods include application of the ADAS-cog assessment, the MMSE assessment, the Montreal cognition assessment or the CERAD methods.

The analyses of sensory function can be applied by using methods known in the prior art to determine threshold values for tastes, odours and sounds, or to determine the ability to differentiate between different odours and tastes.

A person is considered to be mildly frail when it complies with three of the six criterions, and moderately frail when it complies with four criterions or when the score of the three symptoms is so bad, that it seriously impairs the person's condition, as diagnosed by the clinician or physician.

A person is considered to be in nonfrail if none or only one of the six frailty conditions are complied with.

A person is considered to be in a prefrail condition or prodromal frail condition, when his or her condition complies with only two of the six frailty criterions. When the composition according to the invention treats prefrailty, it is defined to act in a preventive manner on the development of frailty. So, prefrailty and prodromal frailty is defined to be synonymous.

A person is defined to be a frail elderly when it complies with the above-mentioned criterions for frailty and in addition is older than 65, preferably 75 years of age.

An individual is defined to be a prefrail elderly when the person's condition complies with the criterions of prefrailty and the person is older than 65, preferably 75 years of age.

Within the context of this invention, when the term "frailty" is used to comprise conditions indicated above as prefrail, prodromal frail, mildly frail or moderately frail.

Though some scientists recognize various forms of frailty, including medical, functional, social, psychological and physical frailty (Faber et al. (2006) Arch Phys Med Rehabil. 87, 885-96), the composition according the invention aims to have its efficacy only in those subjects which comply exactly with the criterions as set above.

Elderly or the aged population is a group that is defined in different ways in the prior art. For the purpose of defining the invention, the inventors have applied the following definition. Elderly or the aged population is defined to be all persons being older than 65 years of age. The "oldest old" are those persons being older than 75 years. The claimed combination for use in accordance with the invention is in particular suitable for treatment of a mammal. In a preferred embodiment, said combination is to be used for the treatment of a human, in particular an elderly person. In the context of this application, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

With the "nutritional management of frail individuals, prefrail individuals and persons experiencing a too low LBM or BMI" according the invention is meant the administration of nutritional components to frail individuals, prefrail individuals or persons having a too low BMI or LBM, in such a way that not only the endogenous concentrations of nutritional components are influenced, but that also the health-beneficial effect is obtained in persons suffering from frailty, frailty symptoms, prefrail persons or individuals suffering from a too low LBM or BMI as claimed in this application. This means that the composition according the invention may induce a concentration in blood of that nutrient, which is outside the normal range as typically observed in the same tissue of healthy individuals, for example of healthy individuals which consume regular food or a normal diet. In the context of this invention, an alternative way of saying the same is that the composition according to the invention also aims to therapeutically nourish frail or prefrail persons or persons having too low LBM or BMI.

It is important to notice that many elderly have become malnourished and have developed deficiencies in one or more nutrients like protein, energy or microingredients or combinations thereof, like PEM (protein-energy malnourishment). Such "malnourishment" is currently assessed by using tools like the "MUST" or "MNA", but it is envisaged by the inventors that alternative tools will be developed, like one that is specifically focussing on nourishment status and one other tool which specifically focuses on general and quick screening of the condition of an individual in order to assess whether a condition is present wherein additional nutrition or other therapy can be useful. Therefore, in one embodiment of the invention the composition according to the invention is used in combination with an assessment of malnourishment of a mammal, preferably using MUST or MNA. In this embodiment, the invention comprises at least the following steps:

1—Assessment of the nutritional status of a mammal, and
2—Intervention with the nutritional or pharmaceutical composition according the invention.

Preferably, the assessment of nutritional status is applied at least twice in combination and relation to the nutritional intervention. More preferably, the assessment is done at least one time before and at least one time after the intervention to measure any changes in nutritional status. The initial nutritional assessment may reveal deficiencies which can be resolved by adapting the intervention composition according to the invention. In order to allow such nutritional management according the invention, separate tools have been defined which is a specific nutritional assessment tool and a module of food components which allows convenient adapatation and fortification of the nutritional intervention composition according to the invention.

A preferred tool for assessing nutritional status comprises several parts, including a questionnaire, which asks the right questions to assess nutritional status, a database which is filled in by answering the questions, and an algorithm which compares the answers with predefined normal values. Optionally conclusions are drawn to arrive at an advice. These functionalities can be incorporated into an electronic device like a computer or minicomputer, by loading and running an appropriate software program. The questions to ask are at least covering biomarkers for the determination of nutrient status using methods as applied in the state of the prior art clinical chemistry laboratories.

Apart from the "nutritional management", the inventors also identify the "therapeutic management" of frailty and prefrailty. In this definition of "therapeutic management", the management of the individual to be treated comprises at least the following steps:

a) diagnosis for frailty, using an assessment of the six criterions defined above for assessing the presence of frailty, b) an intervention using the composition according the invention, and c) measurement of progress made by assessing at least again the same symptom classes as done in step a).

Preferably, the assessment of symptoms is done by using the tool, in particular a form or document or an electronic device loaded with appropriate software, as described below.

Optionally, in the management of frailty and prefrailty, the intervention with the nutritional composition according to the invention can be combined with one or more of 1) an exercise program, 2) a program to improve social interactions, 3) a program to become more exposed to sunlight and fresh air, 4) an adaptation of the diet or of the general food intake practices of the subject, and 5) an intervention with a drug or medicine. It is preferred that the therapeutic management comprises at least a program to be exposed to sunlight and fresh air or an exercise program as a fourth and fifth step in the therapeutic management of the condition of the subject.

In principle, the mammal to be treated may suffer from any of the frailty symptoms as defined above. In particular, the mammal is a human which suffer from at least a neurological or brain problem and one selected from the group of weight loss and an abnormally low physical activity. Preferably, the subject is non-frail or frail. Preferably, the subject has an undesirably low body weight (criterion 5). Preferably the subject does not suffer from dementia, in particular not from senile dementia. For the purpose of the invention, persons that suffer from "senile dementia" are defined as suffering from one or more dementias. Senile dementia or dementia is considered to comprise Alzheimer's disease (AD).

The subject may be a prodromal dementia patient. A "prodromal dementia patient" is a person who does not suffer from a senile dementia as defined above, but has an increased likelihood to develop senile dementia. Likewise, a "prodromal Alzheimer patient" is a person who does not suffer from AD, but has an increased likelihood to develop AD. In principle, any diagnostic tool for determining prodromal dementia patient may be used. Several diagnostic tools that can be used to classify an individual as prodromal dementia patients are described below and include an accurate diagnosis of brain lesions and biochemical problems and careful setting of criteria. Hence, the invention is independently directed at prodromal dementia patients or prodromal Alzheimer's patients.

In particular, persons that score positively on at least one, preferably at least two, more preferably at least three of the following criteria, are considered to be prodromal dementia patients as defined herein:
  a level of more than 350 ng Total-tau per liter cerebrospinal fluid (CSF);
  a weight ratio of abeta-42/Phospho-tau-181 of less than 6.5 in CSF;
  presence of medial temporal lobe (MTL) atrophy, existing of volume loss of hippocampus, entorhinal cortex, or amygdala evidenced on Magnetic Resonance Imaging (MRI) with either qualitative ratings using visual scoring (referenced to well characterised population with age norms) or quantitative volumetry of regions of interest (referenced to well characterized population with age norms)
  presence of fronto-temporal lobe (FTL) atrophy evidenced on MRI with qualitative ratings or quantitative volumetry;
  a level of more than 25 pg F2-iso-prostane (F2-IsoP, isoprostane 8,12-isoiPF2alpha-VI) per mL CSF.

Further explanations of the significance of concentrations of T-tau, P-tau181, Abeta42 and F2-Isoprostane in CSF for future development of Alzheimer's disease can be found in Hansson et al. (2006) Lancet Neurol 5:228-234; and in Pratico et al. (2002) Arch Neurol 59:972-976.

In the context of this document, persons who are in a prodromal state of Alzheimer's Disease (AD) are defined to be in a predementia stage of AD. The values of the biomarkers indicate a condition of the body, in particular the central nervous system, wherein the risk of developing Alzheimer's disease is significantly increased, no matter whether the final form of Alzheimer's disease will be typical Alzheimer's disease, atypical Alzheimer's disease or mixed Alzheimer's disease. This predementia state of the body can be without significant clinical symptoms, the so called preclinical state of Alzheimer's disease, wherein a person is asymptomatic at risk for Alzheimer's disease or is experiencing presymptomatic Alzheimer's disease. It is also important to note that a person may experience mild cognitive impairment without having an increased risk for developing Alzheimer's disease as determined by measuring the above-mentioned parameters (Dubois et al. (2010) Lancet Neurol, 9, 1118-1127).

The composition according the invention has its effects on body weight and/or ADL, no matter the person is a real Alzheimer's disease patient, is a prodromal Alzheimer's disease patient, is a normal elderly which experiences age-associated memory impairment or mild cognitive decline without having increased risk of developing AD, or is in the preclinical state of being at increased risk of developing Alzheimer's disease or a different dementia, like a vascular dementia.

In a specific embodiment, a prodromal Alzheimer patient can be identified as such because he meets at least the first two criteria (total tau and ratio abeta-42/P-tau-181). More preferably, one of the three other criteria (MTL atrophy, FTL atrophy, F2-IsoP) also applies.

In addition to or instead of one or more of the above criteria, the following can be advantageously used:
  reduced glucose metabolism in bilateral temporal parietal areas of the brain, as is detectable by Positron Emission Tomography (PET);
  reduced glucose metabolism in the posterior cingulate cortex, as is detectable by PET;
  impaired blood flow in the brain as measurable by applying Single-Photon Emission Computed Tomography (SPECT), for example by applying the radioisotope 99 mTc-HMPAO);
  impaired glucose metabolism in the brain as measurable by applying SPECT;
  abnormalities in the histology of the medial or inferior temporal lobes as can be determined by MRI or in the rate of glucose utilisation;
  abnormalities in histology or glucose utilization in the temporal parietal cortex or posterior cingulate cortex.

Abnormalities in the condition of the brain or parts thereof can be established by either taking the person's own condition under healthy circumstances as a reference, or, when this is not available, by taking the average condition of a representative group (so matched for e.g. age) as a reference. The latter will occur most frequently. By comparison of an individual's condition with the reference situation and the average situation when the pathological condition would have been developed to its full extent, the clinician is capable of recognizing a prodromal phase. In particular an intermediate situation wherein the individual demonstrates a deviation of x % from the value of a healthy individual in the direction of the pathological conditions is for the purpose of this invention considered to be a prodromal patient. The value of x for the determination of blood flow and glucose metabolism is 20% when determined under standardised conditions in terms of feeding and exercise.

Non-Medical Uses Directed to Body Weight or ADL

A non-medical use according to the invention is directed to increasing or maintaining body weight and/or to improving the ability to perform an activity of daily living of a mammal, for maintaining the ability to perform an activity of daily living of a mammal, or for reducing a deterioration in the ability to perform an activity of daily living of a mammal. This can be accomplished by administering the components used according to the invention, wherein the components are administered to the mammal in a diet without essentially increasing the daily caloric intake of the mammal.

A non-medical use for increasing or maintaining body weight in accordance with the invention, is generally a healthy increase or maintenance of the body weight, i.e. an increase not causing health problems, such as cardiovascular problems.

The subject in a non-medical use may in particular be an elderly human, more in particular a non-institutionalised or independently living elderly human. Preferably the mammal is nonfrail and/or does not have dementia In particular a the use may comprise treatment of a nonfrail human complying with one criterion selected from an undesirably low body mass, having an undesirably low level of daily activity, and having a neurological dysfunction or treatment of a prefrail human having meeting one or two of these criterions.

The skilled person will understand what an undesirably low level of daily activity is, in the context of the present disclosure, see in particular criterion 3. An undesired low degree of physical activity is typically the range of lower 20% of score. In practice this means a PASE score of 55 or less, in particular for men a range of 30-55, preferably 30-45; and for women of 27.5-55, preferably 27.5-45.

The skilled person will understand what an undesirably low body mass is in the context of the present disclosure, see in particular criterion 5 (weight loss).

For instance, for an elderly person a body mass index of less than 23.5 is generally undesirably low.

The elderly person to be treated may in particular have a body mass index in the range of 15-25.0, more in particular in the range of 23.0-25.0. The composition may in particular be used for treating an elderly human to increase BMI to a target value in the range of 23.5 to 28. with the proviso that the target value is higher than the BMI when starting with the use.

It is in particular considered that a use according to the invention is in particular suitable for subjects who have suffered from involuntary weight loss in the year or two years preceding the start of consuming a composition in accordance with the invention. Involuntary weight loss of a subject is weight loss occurring despite the subject's aim to maintain or increase its bodyweight (on the subject's own behalf or after advice of carer or health care professional). Such weight loss can be determined routinely by comparing present weight at with the weight in a period 1-2 years earlier and asking the subject whether he aimed to maintain or increase his body weight. In the case of adult humans, in particular elderly, the subject may in particular be a human, who—when starting with the use, has had an (involuntary) weight loss of 2-4.5 kg in the year preceding the start or 4-6 kg in the two years preceding the start.

The skilled person will understand what a neurological dysfunction is in the context of the present disclosure, see in particular criterion 6 (neurological dysfunction). The dysfunction may in particular be diagnosed using an MMSE assessment. In particular, the frail human having a dysfunction may have an MMSE assessment score below 30, more in particular in the range of 20-26. MMSE can be determined as described by Folstein M F, Folstein S E, McHugh P R. "Minimental state". A practical method for grading the cognitive state of patients for the clinician. J Psychiatr Res 1975; 12:189-98.

In particular a non-medical use for increasing or maintaining body weight comprises one or more of: (i) increasing or maintaining lean body weight and (ii) increasing or maintaining muscle mass. In case the subject is a human, the use preferably comprises increasing or maintaining the body mass index. The non-medical use regarding ADL may in particular be directed at treating a deterioration in ADL as a result of normal aging. It is in particular an aim for such use to contribute to a normalisation of the activities which meets the magnitude of activities which complies with that of age-matched controls. Usually, a non-medical use regarding ADL involves treatment of a subject that has a lowered, yet non-pathological ADL score. In particular, the subject of a non-medical use for improving the ability to perform an activity of daily living of a mammal, for maintaining the ability to perform an activity of daily living of a mammal, or for reducing a deterioration in the ability to perform an activity of daily living of a mammal according to the invention may have a score of more than 2 on the Katz scale, or a PASE score of at least 27.5, in particular in the range of 29-45. In particular, for women the PASE score may be in the range of 27.5-35; in particular. for men, the PASE score may be in the range of 30-35.

The Katz Index of Independence in Activities of Daily Living, commonly referred to as the Katz ADL, is the most appropriate instrument to assess functional status as a measurement of the client's ability to perform activities of daily living independently. Clinicians typically use the tool to detect problems in performing activities of daily living and to plan care accordingly. The Index ranks adequacy of performance in the six functions of bathing, dressing, toileting, transferring, continence, and feeding. Clients are scored yes/no for independence in each of the six functions. A score of 6 indicates full function, 4 indicates moderate impairment, and 2 or less indicates severe functional impairment, see 'M. Wallace et al. 'Try This: Best Practices in Nursing Care to Older Adults, Issue Number 2, revised 2007, from the Hartford Institute for Geriatric Nursing, New York University, College of Nursing' (http://consultgerim.org/uploads/File/trythis/try_this_2.pdf).

The ability to perform an activity of daily living may in particular be selected from the group of abilities to perform light household work (dusting, washing dishes), heavy household work (washing windows, washing floors), number of flights of stair walking, shopping, number of times one raises from his chair, hours sitting in a chair during the day, outdoor gardening, sports activities, paid work activities.

In a non-medical use according to the invention the components are preferably administered to the mammal as part of a nutritional composition, preferably providing a complete nutrition.

Composition According to the Invention

A composition according the invention is a nutritional composition. When referring to nutritional composition, it is understood that such composition has both a nutritional and a medical effect or benefit, i.e. the composition comprises macronutrients which provide a substantial source of energy, other than the active components, in particular proteinaceous matter, fat, other than component (ii), and digestible carbohydrates. It preferably comprises food grade components, which make it suitable for safe oral intake or enteral administration. The components can also be dissolved in a matrix which makes it suitable for parenteral administration. A pharmaceutical composition on the other hand, it is understood that such composition has only a medical effect or benefit, i.e. the composition comprises essentially no ingredients which provide a substantial source of energy, other than the active components.

The composition according to the invention can have any form or physical condition. Preferably, it is a sterile composition or a composition which comprises a defined microorganism population, like a dairy product, for example which is fermented under controlled conditions or a dry product to which probiotics have been added. An example of such fermented product is a yoghurt. The composition according the invention can be solid, semi-solid or a drink. Such forms have been widely disclosed in the prior art. Preferably it is a drink, though for mammals which experience dysphagia, a highviscosity product or a semi-solid form is preferred.

The composition according to the invention may also be a kit-of-parts comprising the components according to the invention, packed for simultaneous or sequential administration to a person in need thereof. Hence, each component may be packed separately, or some may be packed together, for example in a sachet, bottle, etc.

The composition according the invention is preferably a composition which complies with the criterions as set for the ruling regulations for food for special medical purposes or of a medical food. These regulations are distributed by the Food and Drug Administration or as directives from the European Union or by recognized authorities in other jurisdictions. In particular the composition according to the invention provides those nutrients and those amounts as required by the mammal because of the specific disease state of the mammal. These amounts of the active components cannot be consumed by adapting the normal diet.

In an embodiment, the composition according the invention is meant to therapeutically improve one or more of body weight, body mass index, lean body weight, muscle mass, muscle strength or muscle function. This improvement can occur in elderly, in particular frail elderly. The composition according to the invention can suitably be used in the nutritional management of individuals suffering from frailty symptoms or the therapeutic management of frailty (or pre-frailty), by providing a certain amount of the active components per day, and preferably per period of about 4 hours.

A daily amount as described herein means in particular an amount in a daily dosage unit provided by the combination of the invention. Such a daily dosage unit may be a single dosage, but it may also be divided over two or three, or even more daily servings. If the combination, according to a preferred embodiment, is intended for administration as a single unit, the daily amounts as described herein are preferably the amounts present in the (preferably packaged) combination unit.

It has been found that the administration of at least two components selected from the group of (i) a nucleoside equivalent, (ii) an ω-3 polyunsaturated fatty acid selected from the group of DHA, DPA and EPA, (iii) a vitamin B selected from the group of vitamin B6, B11 and B12, (iv) a phospholipid, (v) an antioxidant, preferably selected from the group of vitamin C and vitamin E and (vi) a choline, with the proviso that at least component (i) or (iii) is present, is suitable for use in the prevention or treatment of frailty in a mammal, in one embodiment together with or as part of a diet providing energy sources (carbohydrate, protein, fat), compared to the same isocaloric diet without said combination. Thus, it is concluded that the composition according to the invention is effective, without needing an increase in caloric intake. Accordingly, in a specific embodiment, the effect of said combination on increasing one or more of body weight, body mass index, or lean body weight is not attributed to an increase in caloric intake.

(i) Nucleoside Equivalent

The composition according to the invention may comprise a nucleoside equivalent. As used herein, nucleosides include nucleosides as such deoxynucleosides as such, and equivalents of nucleosides as such or deoxynucleosides as such. Thus, when referring to a nucleoside, this term is meant to include the corresponding deoxynucleoside.

Equivalents in particular are compounds comprising a nucleobase, such as mononucleotides (mono-, di- or triphosphates of nucleosides), oligonucleotides, polynucleotides, nucleobases and physiologically acceptable derivatives thereof that may be converted into the nucleoside as such or a nucleotide as such in vivo. Examples of such derivatives include various esters. WO 2002/088159 (Trommsdorff GmbH) relates to uridine esters, which may be used in accordance with the present invention. The contents of this publication regarding (deoxy)uridine esters is incorporated by reference. Such equivalents are capable of increasing endogenous levels of the active forms of nucleosides in body tissues such as blood, liver and brain. Also synthetic compounds can be suitably included as nucleoside source, e.g. acylated derivatives of the nucleosides, for example triacetyluridine.

The composition according to the invention preferably comprises a pyrimidine nucleoside or equivalent thereof, such as cytidine or equivalent thereof or a uridine or equivalent equivalent. More preferably, the composition according to the invention comprises a uridine or an equivalent thereof, preferably at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. Preferably, the composition according to the invention comprises an uridine phosphate selected from uridine monophosphate (UMP), uridine diphosphate (UDP) and uridine triphosphate (UTP). Most preferably, the composition according to the invention comprises UMP, as UMP is most efficiently being taken up by the body after oral administration. Hence, inclusion of UMP in the composition according to the invention enables a high efficacy at the lowest dosage, the administration of a low volume to the subject or both. Uridine derivatives like UDP, which is readily formed from dietetic UMP, also appear to be important, in particular for trans-port of glycoproteins and glycolipids within the cell and availability thereof in the cytosol and plasma membrane.

Preferably, at least 20 weight % of the uridine or an equivalent thereof in the composition according to the invention is provided by UMP, more preferably at least 50 weight %, most preferably at least 90 weight %.

Preferably, the present use comprises the daily administration of uridine or an equivalent thereof in a daily dosage of 0.08 to 3 g per day, preferably 0.1 to 2 g per day, more preferably 0.12 to 1 g per day.

Preferably, the present use comprises the daily administration of UMP in a daily dosage of 1.3 to 37.5 mg UMP per kilogram body weight of the subject to be treated. The required dosages of the equivalents of uridine on a weight basis can be calculated from the daily dosage for UMP by taking equimolar amounts using the molecular weight of the equivalent and of UMP, the latter being 324 Dalton. The daily dosage of equivalents is preferably 3 to 115 μmol per kg body weight per day, preferably 5 to 35 μl per kg body weight per day, or 0.25 to 9 mmol, preferably 0.3 to 6, most preferably 0.45 to 2.8 mmol per day.

Preferably, the present use comprises the daily administration of a combination comprising uridine or an equivalent thereof in an amount of 0.06 to 2.4 g UMP per 100 ml liquid composition, preferably 0.08 to 1.6 g UMP per 100 ml liquid composition, more preferably 0.12 to 0.8 g per 100 ml liquid composition. Alternatively, the optimal dose for uridine monophosphate per 100 g dry matter is 0.18 to 7.2 g, preferably 0.24 to 5.4 g and more preferably 0.36 to 2.4 g.

As a suitable cytidine equivalent cytidine can be used, for example as free base or as a salt, as an ester, as a phosphate derivative, like CMP, CDP or CTP, as cytosine, and as choline derivative, e.g. as citicoline. However, when both an uridine equivalent and a cytidine equivalent are included simulateously in the composition according to the invention it is preferred that the weight ratio of the sum of uridine and equivalents thereof to the sum of cytidine and equivalents thereof is larger that 1.0, more preferably at least 2.0, most preferably more than 5.0. Although cytidine is a precursor of uridine, it is more efficient and effective to include uridine in the composition according to the invention, because it passes more easily the blood brain barrier.

In some embodiments of the invention, useful sources of nucleosides include extracts of plant, animal, bacterial, algae or yeast material, e.g. in a composition according to the invention for individuals which don't suffer from a kidney disease. Examples of such extracts include heat-treated aqueous extracts from baker's yeast or brewer's yeast. In a further preferred embodiment, the composition according to the invention preferably does not contain high amounts of other nucleotides. Hence, preferably the weight ratio sum of uridine and equivalents thereof to adenosine or its equivalents in the composition according to the invention is below 0.1, more preferably below 0.01, most preferably 0. Preferably, the weight ratio of the sum of the amount of uridine and equivalents thereof to the amount of guanosine or its equivalents in the composition according to the invention is below 0.1, more preferably below 0.01, most preferably 0. Preferably, the weight ratio of sum of uridine and equivalents thereof to inosine in the composition according to the invention is below 0.1, more preferably below 0.01, most preferably 0.

(Ii) ω-3 Polyunsaturated Fatty Acids (ω-3 PUFA's)

The composition according to the invention may comprise an ω-3 polyunsaturated fatty acid (ω-3 PUFA), in particular an ω-3 long chain polyunsaturated fatty acid (LCPUFA), more in particular selected from the group of docosahexaenoic acid (22:6 ω-3; DHA), docosapentaenoic acid (22:5 ω-3; DPA) and eicosapentaenoic acid (20:5 ω-3; EPA). Useful sources include fish oil, algae oil, eggs lipids and genetically modified organisms.

Preferably, the composition according to the invention comprises at least DHA, preferably DHA and EPA. More preferably, the combination comprises DHA and at least one precursor of DHA selected from EPA and DPA. More preferably, the composition according to the invention comprises DHA and EPA. The inventors recognized that only a part of the DHA incorporated in the brain originates from orally ingested DHA. An important part of the DHA incorporated in the brain is derived from conversion of DPA to DHA in the brain. In a further aspect, the composition according to the invention preferably contains a significant amount of EPA. EPA is converted to DPA (ω-3), increasing subsequent conversion of DPA (ω-3) to DHA in the brain. Hence, the composition according to the invention preferably also contains a significant amount of EPA, so to further stimulate in-vivo DHA formation.

The ω-3 PUFA's, in particular the LCPUFA's, more in particular DHA, DPA and EPA, may be provided in any form such as, but not limited to, triglycerides, diglycerides, monoglycerides, free fatty acids or their salts or esters, phospholipids, lysophospholipids, glycerol ethers, lipoproteins, ceramides, glycolipids or combinations thereof. Preferably, the composition according to the invention comprises at least DHA in triglyceride form.

Preferably, the present method comprises the daily administration of 200 to 5000 mg, more preferably 400 to 3000 mg, most preferably 800 to 2500 mg of the sum of DHA and EPA. The proportion of (DHA+EPA) relative to the total amount of fatty acids in the combination is preferably 5 to 50 weight %, more preferably 10 to 45 weight %, most preferably 15 to 40 weight %. Preferably, the present method comprises the daily administration of 100 to 4000 mg, more preferably 120 to 1800 mg of DHA.

Preferably, the composition according to the invention comprises 1 to 40 weight % DHA based on total amount of fatty acids, preferably 3 to 36 weight % DHA based on total amount of fatty acids, more preferably 10 to 30 weight % DHA based on total amount of fatty acids in the composition according to the invention. The composition according to the invention preferably comprises 0.5 to 20 weight % EPA based on total amount of fatty acids, preferably 2 to 10 weight % EPA based on total amount of fatty acids, more preferably 5 to 10 weight % EPA based on total fatty acids. The weight ratio of DHA to the sum of EPA and DPA is preferably larger than 1.0, more preferably 1.2 to 10, more preferably 2 to 8. The above-mentioned ratios and amounts take into account and optimise several aspects, including taste (too high LC-PUFA levels reduce taste, resulting in a reduced compliance), balance between DHA and precursors thereof to ensure optimal effectiveness in relation to maximum dosage and possibility of product formulations such as liquid form, bar or capsule.

In one embodiment, the composition according to the invention contains a low amount of arachidonic acid (AA; 20:4 ω-6). Arachidonic acid is believed to counteract the effects of the composition according to the invention. The present subjects normally ingest sufficient AA, or precursors thereof, and an excess daily dosage may stimulate inflammatory responses, inhibiting daily activities. Preferably, the weight ratio DHA/AA in the composition according to the invention is at least 5, preferably at least 10, more preferably at least 15, up to e.g. 100. Preferably, the weight ratio EPA/AA is at least 2. The present method preferably comprises the administration of a composition comprising less than 5 weight % AA based on total amount of fatty acids, more preferably below 2.5 weight %. The ω-6/ω-3 weight ratio of long-chain polyunsaturated fatty acids with at least 20 carbon atoms in the composition according to the invention is advantageously below 0.5, preferably below 0.2. If the long-chain polyunsaturated fatty acids with 18 carbon atoms are also included in the ratio, the preferred ω-6/ω-3 weight ratio is 0.05 to 1, more preferably 0.1 to 0.6, most preferably 0.15 to 0.4.

(iii) Vitamin B

In an embodiment, the composition according to the invention comprises at least one vitamin B selected from the group of vitamin B6, vitamin B9 and vitamin B12. Vitamin B6 includes pyridoxine, pyridoxal, pyridoxamine, and pyridoxine salts, e.g. the hydrochloride or phosphate salt. Vitamin B9 is also known as folic acid or folate. Vitamin B12 is also known as cobalamines.

In particular, good results have been achieved with a combination comprising vitamin B6, vitamin B12 and vitamin B9. Advantageously, vitamin B12 and vitamin B9 are included because low plasma B12 or vitamin B9 levels are a risk factor for the development of Alzheimer's disease.

It should be noted that one or more other vitamins of the vitamin B family may be present in a composition (for use) according to the invention, that do not form part of the active components mentioned under '(iii) vitamin B' for use in accordance with the invention. Such other vitamins B include in particular vitamin B1 (thiamine), vitamin B2 (riboflavin), vitamin B3 (niacin or niacinamide), vitamin B5 (pantothenic acid), and vitamin B7 (biotin).

The vitamin B is to be administered in an effective dose, which dose depends on the type of vitamin B used. As a rule of thumb, a suitable minimum or a maximum dose may be chosen based on known dietary recommendations, for instance as recommended by Institute of Medicine (IOM) of the U.S. National Academy of Sciences or by Scientific Committee on Food (a scientific committee of the EU), the information disclosed herein and optionally a limited amount of routine testing. A minimum dose may be based on the estimated average requirement (EAR), although a lower dose may already be effective. A maximum dose usually does not exceed the tolerable upper intake levels (UL), as recommended by IOM.

If present in the nutritional or pharmaceutical composition according to the invention, the vitamin B6 is usually present in an amount to provide a daily dosage in the range of 0.5 to 100 mg, in particular in the range of 0.75 to 25 mg, more in particular in the range of 0.9 to 5 mg If present in the nutritional or pharmaceutical composition according to the invention, the vitamin B12 is usually present in an amount to provide a daily dosage in the range of 0.5 to 1000 μg, in particular in the range of 1 to 100 μg, more in particular in the range of 1.5 to 10. If present in the nutritional or pharmaceutical composition according to the invention, the vitamin B9 is usually present in an amount to provide a daily dosage in the range of 50 to 5000 μg, in particular in the range of 150 to 1000 μg, more in particular in the range of 200 to 1000 μg In a preferred embodiment of the invention, the active components are included in a drink, preferably having a volume of about 125 ml, or in an alternative preferred embodiment in a product having a dry mass content of about 30 g, per packaging each of them being for consumption once a day. This means that the amounts per daily dose as mentioned above can be recalculated to a concentration per milliliter, by dividing the above-mentioned value with 125, or to a concentration per g dry mass of the product by dividing by 30.

This way of calculation also applies to the other active components (i) to (vi) in the composition according to the invention when a desired dose per daily dose is disclosed.

(iv) Phospholipids

The composition according to the invention may comprise a phospholipid. As used herein, the term phospholipid includes lyso-phospholipids, de-acylated phospholipids and glycerophospholipids. It is preferred to include a phospholipid which is capable of increasing chylomicrons formation in elderly after administration of triglyceride lipids and can provide useful fatty acids. In particular, the phospholipid is selected from the group of phosphatidylcholine (PC), phosphatidylethanolamine (PE), phosphatidylserine (PS), phosphatidic acid (phosphatidate), phosphoinositides (such as phosphatidylinositol (PI), phosphatidylinositol phosphate, phosphatidylinositol bisphosphate, phosphatidylinositol triphosphate) and sphingomyelin. In particular, the combination according to the invention comprises at least two different phospholipids selected from the group consisting of phosphatidylserine, phosphatidylinositol, phosphatidylcholine and phosphatidylethanolamine. Preferably the combination according to the invention comprises phosphatidylcholine, phosphatidylethanolamine and phosphatidylserine. Good results have been achieved with a combination of phosphatidylcholine (PC) and phosphatidylserine (PS), preferably in a weight ratio of 3:1.

For instance, lecithin may be used as a source for the phospholipids. Optionally the phospholipids are fortified with one or more phospholipids, such as a ceramide, a sphingolipid or a specific phospholipid, such as a phosphatidylcholine.

The phospholipid is to be administered in an effective dose. Usually, the total phospholipid daily dosage is in the range of 50 to 5000 mg, in particular in the range of 100 to 2000 mg, more in particular in the range of 150 to 1200 mg Inclusion of phospholipids further beneficially improves membrane function, thereby enabling an improved functioning of the different parts of the brain that may be affected in prodromal subjects. Furthermore, the phospholipids improve stability and shelf life of the composition according to the invention. Phospholipids further enable the manufacturing of palatable compositions. Also, phospholipids are a source for choline and prevent the decline in plasma choline levels after exercise. Choline is necessary for the formation of acetylcholine, a neurotransmitter involved in learning and memory and in the activation of muscles. These advantages are already achieved at relatively low phospholipid levels.

(v) Anti-Oxidant

The composition according to the invention may comprise an antioxidant selected from the group of vitamin C, vitamin E and selenium. The vitamin C may be present as free acid (ascorbic acid) or as a salt, e.g. sodium ascorbate or potassium ascorbate. Suitable sources of vitamin E include (alpha-) tocopherol and tocotrienol. Suitable sources of selenium include selenate and selenite.

The anti-oxidant is to be administered in an effective dose. As a rule of thumb, a suitable minimum or a maximum dose may be chosen based on known dietary recommendations, for instance as recommended by the Institute of Medicine (IOM) of the U.S. National Academy of Sciences or by the Scientific Committee on Food (a scientific committee of the EU), the information disclosed herein and optionally a limited amount of routine testing. A minimum dose may be based on the estimated average requirement (EAR), although a lower dose may already be effective. A maximum dose usually does not exceed the tolerable upper intake levels (UL), as recommended by IOM. If present in the combination, vitamin C is usually present in an amount to provide a daily dosage in the range of 20 to 1200 mg, in particular in the range of 30 to 400 mg, more in particular in the range of 35 to 120 mg. If present in the nutritional or pharmaceutical composition according to the invention, the vitamin E is usually present in an amount to provide a daily dosage in the range of 8 to 200 mg, in particular in the range of 20 to 140 mg, more in particular in the range of 35 to 100 mg.

If present in the nutritional or pharmaceutical composition according to the invention, the selenium is usually present in an amount to provide a daily dosage in the range of 40 to 400 μg, in particular in the range of 50 to 200 μg, more in particular in the range of 55 to 80 μg.

Optionally one or more antioxidants may be present other than (v) the antioxidant selected from the group of vitamin C, vitamin E and selenium.

(vi) Choline

The nutritional or pharmaceutical composition according to the invention may comprise a choline. Choline refers to the various quaternary ammonium salts containing the N,N,N-trimethylethanolammonium cation. More specifically, choline is selected from the group of the choline cation, choline salts or esters, such as choline chloride, choline bitartrate, choline stearate, or the like, or compounds that dissociate to choline, such as choline alfoscerate, sphingomyelin, cytidine-diphospho-choline or citicoline or CDP-choline, acylglycerophosphocholines, e.g, lecithin, lysolecithin, glycerophosphatidylcholine, and any mixture thereof. It is preferred to include a choline salt or choline alfoscerate into the composition according to the invention.

In particular, choline is to be administered in an amount to provide a daily dosage of 100 to 4000 mg, more in particular of 200 to 2000 mg.

Furthermore, the nutritional or pharmaceutical composition according to the invention may comprise one or more further micronutrients, for instance one or more micronutrients selected from the group of vitamins, minerals, and trace elements, taurine and inositol.

Protein and Energy Content

The composition, preferably the nutritional composition according to the invention allows improvement of BMI, or LBM, or frailty, without demanding to consume large amounts of protein or additional energy. Actually, the amount of energy in the composition according to the invention can remain limited to a value of less than 400 kcal (1680 kJ), preferably less than 280 kcal (1178 kJ) or more preferably less than 210 kcal (882 kJ), all expressed per daily dose for an adult human. The amount of energy is not needed to create the effect (as can be concluded from the experiment, which has an isocaloric control), but is simply the result of incorporating the active components into a small sized food product, which is thus used as a vehicle. In one embodiment, the components (i) to (v) are included in a pharmaceutical composition according to the invention having an energy content per serving unit of less than 130 kcal (546 kJ) or preferably less than 80 kcal (336 kJ).

In one embodiment, the amount of active components (defined as components (i) to (v)), which is needed to achieve the effect on BMI, etc, delivers more than 50%, preferably more than 58%, most preferably 62 to 88% of the total amount of calories of the composition as claimed. For the calculation of energy, the inventors use 9 kcal (37.8 kJ) per g of lipids or phospholipids, zero kiloJoule per g of nucleosides, vitamins and a choline equivalent, 4 kcal (16.8 kJ) per g of protein and digestible carbohydrate and 2 kcal (8.4 kJ) per g of fibre.

The protein amount in the composition according to the invention, if present, can remain relatively low, which can have important advantages to the largest part of individuals which suffer from weight loss or symptoms of frailty. In particular, it is preferred that composition according to the invention should not impair normal eating patterns, allow manufacture of a palatable product and not induce heartburn or gastrointestinal discomfort after consumption thereof. The composition according the invention appears effective, also when the concentration of protein in the composition according to the invention remains below 11 g per 100 ml and preferably below 9, more preferably 3 to 8.4 g, and most preferably 5.2 to 8.2 g per 100 ml of the composition according to the invention.

For concentrates, semi-dry and dry products, it is more convenient to express the concentration of protein on gram dry matter basis. The amount of protein is in these cases usually less than 400 mg, preferably less than 360 mg, more preferably 100-340, most preferably 150 to 330 mg per g dry matter. Simple proteins can be used in these amounts like milk protein. These technical features of the composition according to the invention result in good compliance with the feeding protocol with such composition according to the invention and in very little adaptation of the normal diet after the composition according to the invention have been consumed according their recommended use.

In order to avoid an undesired satiating effect, especially in elderly, the amount of caseinates preferably is 4.5 weight % or vol % or less for liquid formula, and more preferably 0.5 to 4.0 weight % or vol % or most preferably 0.8 to 3.3 weight % or vol %. Therefore, but also for efficacy reasons, it is preferred to include a non-caseinate in the composition according to the invention, which is elaborated below.

The effect of the active components (specific combinations of nucleosides, LC-PUFAs, phospholipids, vitamins and a choline equivalent) allows efficacy by administering a nutritional composition according to the invention with the minimum amount of food volume, e.g. less than 150 ml per serving unit, which is also important because elderly, and especially frail elderly experience much earlier satiety when consuming food.

In one embodiment of the invention the actives are provided to the consumer, in a ready to use serving unit which provides 15 to 160 g of the effective composition according to the invention.

It has been suggested before, that additional protein of specific quality could improve LBM or increase body weight in elderly. Focus in the most relevant papers in this field is on the amount of protein (which should preferably be more than a few dozen g additional protein per daily dose), inclusion of L-leucine or including a large portion of essential amino acids in the protein amount, e.g. more than 15 g of the pure crystalline amino acids. Complying to such diet can be very demanding to many frail elderly, also because the taste of free amino acids is often considered as offensive or because consumption of such large amounts of protein has a significant impact on the consumption of regular diet.

The invention therefore provides a solution for the problem that an undesired amount of additional protein has to be administered for anabolic purposes, i.e. the improvement in BMI of elderly and it increases the improvement of the brain function as observed in frail elderly by consuming the combination of one or more of the active components (i) to (v) according to the invention.

The protein amount preferably comprises a non-caseinate protein for supporting an effect of the composition according the invention on BMI in frail elderly. In particular, specific whey protein relatively low in phosphorous, fish proteins, in particular cod protein, or a protein derived from eggs and proteins derived from vegetables, like potato, soy, pea, beans, lupin, quinoa and amaranth appeared suitable. The proteins can be intact, either heat-treated or non-denatured, or be partially hydrolyzed. Hydrolyses of the intact protein aims to improve its solubility, but degree of hydrolyses should be kept to the minimum, preferably to a degree of hydrolyses between 2 and 12, in order to maintain good organoleptic properties of the ready to use composition according to the invention. In a preferred embodiment, the amount of non-dairy protein is more than 21 weight %, more preferably more than 25 weight %, most preferably more than 42 weight %, in particular more than 51 weight % of the protein amount.

Suitable whey proteins include those which have a phosphorous content less than 400 mg/l when 100 g of the protein is dissolved in one liter of water. Preferably, this phosphorous content is 70 to 340 mg/l. The amount of protein can be calculated from the label of the product, or, when this is impossible or not justified by measuring Kjeldahl nitrogen by a method accepted as preferred in the prior art for the specific matrix, and multiplying this by 6.25 for mixtures of proteins and peptides.

If dairy proteins are included, it is preferred to include a whey protein. Such protein is preferably enriched in serum albumin or alpha lactalbumin. Such dairy amount also preferably comprises a lactoferrin. The concentration of alpha-lactalbumin as fraction of all whey proteins is preferably more than 25 weight %, that of serum albumin 5 to 12 weight %. The concentration of lactoferrin is preferably in the range 0.25 to 3 weight %, preferably 0.29 to 1.4 weight %, more preferably 0.34 to 1.2 weight % of the protein amount.

In cases where the fatty acids comprise that much omega 3 fatty acids that the ratio of the weight amounts of omega 3 to omega 6 exceed 5, the amount of whey protein is preferably less than 50 weight % of the protein amount, in order to keep the satiating character of the composition according to the invention as low as possible, while maintaining efficacy of the composition according to the invention.

It is also useful to include non-essential amino acids or their salts or esters. Examples of suitable amino acids include serine and aspartic acid. These amino acids can be administered as L-isomer or as a racemic mixture of L and D isomers of the particular amino acid. The amount aspartate plus asparagine in the composition according to the invention is preferably more than 8.4, more preferably 9.0 to 16, most preferably 9.5 to 15 g per 100 g amino acids in the composition according to the invention. The amount of serine in the ready to use composition according to the invention is preferably more than 4.1 g per 100 g amino acids. The presence of these two amino acids in the formula is thought to be at least partially responsible for the anabolic character of the formula and the observed efficacy in treating symptoms of frailty. Increasing the concentrations to the indicated amounts in the preferred embodiment increases their effect. In this respect, the effect on neurological symptoms in the low BMI elderly includes the effect on depressed mood, stamina and the activities of daily living. The inventors believe that an effect on metabolic pathways is responsible for this, in particular an effect on glucose metabolism and gene expression and not the amount of calories or amount of protein that are provided by the composition according the invention.

The selected types and amounts of protein appeared to have the unexpected advantage in that long term administration to persons experiencing frailty or low body weight, especially in the aged population achieved better results in increasing BMI, lean body mass or body weight and muscle function, muscle strength and muscle mass, than most high protein dairy protein based formula, fortified with essential amino acids, and demonstrated less adverse effects in sensitive persons.

It is of importance that in a preferred embodiment, the protein amount contributes to a better functioning of metabolism in order to support the maintenance of BMI, and lean body mass, and other symptoms of frailty, like exhaustion and fatigue and neurological function. Therefore, the protein preferably comprises a whey protein and more preferably a whey protein and a vegetable protein.

In a preferred embodiment, the osmotic value of the composition according to the invention is as low as possible, in order to facilitate easy stomach emptying. In a preferred embodiment, the composition according to the invention demonstrates an osmolality below 450 mEq/l.

In addition, the buffer strength of the composition according to the invention preferably low, in order to achieve rapid digestion and gut transfer of the composition according to the invention after consumption. This is done by using the amounts and types of proteins as indicated above and by preventing the use of high salt loads, in particular of citrates and phosphates. The amount of phosphorous in the composition according to the invention is preferably less than 150 mg, more preferably 20 to 110 mg, most preferably 50 to 72 mg per 100 ml. In one embodiment, the nucleotides in the composition according to the invention, like a uridine phosphate, or cytidine phosphate are replaced by their base. In a preferred embodiment, the composition according to the invention comprises a nucleobase and a nucleoside or nucleotide. In a preferred embodiment, the ratio of the weight amount of nucleobase to the sum of the corresponding nucleosides and nucleotides is more than 0.06, preferably 0.2 to 0.9.

The amount of organic acids, like citrates, is preferably less than 2, more preferably less than 1.2 weight %, most preferably 0.1 to 0.9 weight % of the digestible carbohydrate amount. These features are in particular relevant when the elderly suffer from diagnosed anchlorhydria. This is a major problem in elderly and in particular in institutionalized elderly or elderly having a BMI under 23.5 kg/m2 or frail elderly.

In a preferred embodiment, the composition according the invention is a liquid formula having a viscosity of less than 60, more preferably 2 to 30 mPa·s, measured at 20 degrees ° C. As used herein, the viscosity is the viscosity as measurable using a Anton Paar Physica MCR301 rheometer with aCP50-1/PC cone (diameter 50 mm, 1° difference between middle and outside) at 20° C. at 100 s$^{-1}$.

Dosage Form

Further, one or more additional ingredients may be present that are commonly used in the prior art, dependent on the form—nutritional or pharmaceutical composition—in which the combination is provided.

If the dosage form is a pharmaceutical composition, the pharmaceutical composition may comprise one or more excipients known in the prior art to provide a pharmaceutical composition in a dosage form of choice. The pharmaceutical composition is preferably for enteral application (orally or via tube-feeding). Examples of solid formulations are tablets, capsules (e.g. hard or soft shell gelatine capsules), pills, sachets, powders, granules and the like which contain the active ingredients together with a conventional carrier. Any conventional carrier material can be utilized. The carrier material can be organic or inorganic inert carrier material suitable for oral administration. Suitable carriers include water, gelatine, gum Arabic, lactose, starch, magnesium stearate, talc, vegetable oils, and the like. Additionally, additives such as flavouring agents, preservatives, stabilizers, emulsifying agents, pH-buffers and the like may be added in accordance with accepted practices of pharmaceutical compounding. While the individual active ingredients are suitably administered in a single composition they may also be administered in individual dosage units.

If the dosage form is a nutritional composition, the composition generally comprises at least one macronutrient for providing (additional) energetic value to the nutritional composition. The macronutrient may suitably be selected from the group of proteinaceous matter (proteins, peptides, amino acids), fat, other than component (ii), and digestible carbohydrates.

Suitable proteinaceous matter, lipids and carbohydrates, and suitable concentrations of the macronutrients may be based on known dietary guidelines for food products, in particular for food products for the elderly. Suitable formulations may e.g. be based on known commercially available clinical foods, or foods advertised for feeding elderly people or for feeding people suffering from dementia.

Regarding the lipid, preferably one or more triglycerides are present. These may be selected from vegetable oils and fats and animal oils and fats.

Regarding the digestible carbohydrates, these may in particular be selected from digestible pentoses, digestible hexoses digestible oligosaccharides, e.g. digestible disaccharides and digestible trisaccharides. and digestible polysaccharides (e.g. starch). More specifically one or more digestible carbohydrates may be chosen selected from the group of galactose, mannose, ribose sucrose, trehalose, palatinose, lactose, maltodextrose, maltose, glucose, fructose, including oligomers and polymers thereof.

Optionally, a nutritional composition according to the invention comprises one or more non-digestible carbohydrates (dietary fibres) such as oligosaccharides. As used herein, the term oligosaccharides in particular refers to saccharides comprising 3 to 25 monosaccharide units per molecule. The oligosaccharide(s) may in particular be selected from the group of fructo-oligosaccharides (FOS), galacto-oligosaccharides (GOS), trans-galacto-oligosaccharides (TOS), xylo-oligosaccharides (XOS), soy oligosaccharides, and the like. Optionally, also higher molecular weight compounds such as inulin, resistant starch and the like may be incorporated in the composition according to the invention.

Further, the nutritional composition may comprise a probiotic.

Further, the nutritional composition may comprise one or more additives commonly used in food technology, such as one or more additives selected from the group of flavourings, stabilisers, preservatives, colourants, emulsifiers, pH-buffers etc.

The nutritional composition for use in a accordance with the invention may be a solid composition. a semi-solid composition (such as a paste or a gel) or a liquid composition, such as a beverage of a drinkable food product.

The nutritional composition according to the invention may in particular be intended for enteral administration (orally or by tube feeding). Alternative forms of administration may be applied, in particular parenteral administration. The skilled person will be able to formulate a suitable product for parenteral administration, in particular by preventing inclusion of non-endogenous proteinaceous material which may induce an allergic reaction or other adverse effects. The administration may be carried out based on a manner known per se for a specific type of nutritional composition.

In particular, the nutritional composition may be selected from the group of spreads; yoghurts, custards, ice-creams, butter, and other dairy products; dairy-substitute products; drinks, such as fruit drinks; candy bars; cookies, cakes and other bakery products; and drinkable foods.

The total energetic value of the composition may be chosen within wide limits and may range, e.g., from 0.2 to 4 kcal/g. In particular, the energetic value may be at least 0.4 kcal/g, more in particular at least 0.8 kcal/g. In particular, the energetic value may be 5 kcal/g or less, more in particular 3 kcal/g or less.

In case the nutritional composition is a fluid, it usually has a nutritional value of at least 20 kcal/100 ml, preferably of at least 50 kcal/100 ml, in particular of at least 75 kcal/100 ml or at least 100 kcal/100 ml. For a fluid composition the nutritional value is usually 300 kcal/100 ml or less, in particular 200 kcal/100 ml or less, more in particular 150 kcal/100 ml or less.

Suitable dosage forms, active ingredients, further components that may be coadministered and ways of administration are as described for the nutritional or pharmaceutical composition as described herein above, the claims, or the examples herein below.

The vitamin B, the phospholipid, the antioxidant and—if present—further active ingredients, may be administered under the supervision of a medical specialist or be self-administered.

Specific Embodiment

Nutritional Composition (Per Se)

As mentioned above, the invention also relates to a nutritional composition comprising (i) at least one component selected from the group of uridine and iuridine monophosphate, (ii) DHA and EPA (which may be present in bound for e.g. as a triglyceride ester) (iii) a vitamin B, (iv) a phospholipid, v) an antioxidant, and (vi) a choline. Preferred sources, preferred specific compounds for each group, concentrations, dosages and other product properties may generally be as described herein above. The nutritional composition according to the invention usually also comprises, protein. Further, digestible carbohydrate and fibre. are usually present. Preferably, the nutritional composition comprises i-a) the nucleoside uridine and i-b) the nucleotide uridine monophosphate. i-a) Uridine and i-b) uridine monophosphate are preferably present in a weight to weight ratio in the range of 0.2:1 to 0.7:1. The presence of both i-a) uridine and i-b) uridine monophosphate, especially in said ratio, is in particular advantageous because it provides a more uniform bioavailability after oral administration, which increases the number of responders to the composition (used) according to the invention (subjects reacting positively on treatment with a composition in accordance with the invention), without any unacceptable adverse effects. In addition, the nucleoside uridine may decreases activation of P2Y receptors in the gut.

In a preferred embodiment, the total content of uridine plus uridine monophosphate is in the range of 5-30 mg per gram dry weight, more preferably in the range of 8-20 mg per gram dry weight, in particular in the range of 10-18 mg per gram dry weight.

The total content of uridine plus UMP as a weight percentage of total nucleoside equivalents preferably is more than 28 wt. %, more preferably 40-100 wt. %, most preferably 60-100 wt. %, in order to obtain a selective effect of the nucleotide fraction in the product of the invention, such as in order to avoid triggering an undesired effect in the enterocytes or liver or the enteral nervous system, due to activation of receptors, for example the P2X or P2Y receptors, by adenosine-based or guanosine-based nucleotides.

The weight to weight ratio of UMP to GMP (guanosinemonophosphate) preferably is more than 10. The weight to weight ratio of UMP to UMP (inosine monophosphate preferably is more than 10.

In a specific embodiment, the nutritional composition according to the invention, comprises 3-14 mg EPA per gram dry matter, preferably 5-10 mg EPA per gram dry matter and 12-56 mg DHA per gram dry matter, preferably 2.5-20 mg DHA per gram dry matter. Preferably, the sum of DHA and EPA is 5-50 wt. % based on total fatty acids.

A composition according to the invention preferably has a low arachidonic acid (AA), content, if present at all, especially in an embodiment wherein on or more of component (ii) ω-3 PUFAs selected from EPA, DHA and DPA are present. AA is thought to have a disadvantageous effect on the effectiveness of these components in a use according to the invention. In view thereof, the weight to weight ratio of the sum of DHA+DPA+EPA to AA preferably is higher than 5, in particular 6 or higher, more in particular 12 or higher. In a particularly preferred embodiment, the weight to weight ratio of DHA to AA is higher than 5. The ratio long chain ω-6 PUFAs to long chain ω-3 PUFAs preferably is 0.05 to 1. The term 'long-chain' is used herein for PUFA's having a carbon chain of at least 20 carbon atoms.

The ratio [uridine monophosphate+uridine]/[phospholipds] of a nutritional composition according to the invention is usually less than 5.9, preferably 0.15-4, in particular 0.20-2.4, more in particular 0.25-0.71. A relatively low ratio of [uridine monophosphate+uridine]/[phospholipds] is in particular preferred in a composition comprising a protein. In particular in such embodiment, it contributes to a better efficacy with respect to a use of the invention, in particular with respect to providing a palatable effective product a decrease of uridine concentration and an increase of phospholipid concentration allows better tasting while maintaining efficacy. A relatively low ratio is also is advantageous for improving the palatability, especially during shelf-life.

The nutritional composition of the invention usually has an energy density of less than 13 kcal per gram dry matter, preferably of 3-9.3 kcal per gram dry matter, more preferably of 4.0-7.0 kcal per gram dry matter.

In a specific embodiment, the nutritional composition according to the invention, comprises phosphatidylcholine (PC). In such embodiment the weight to weight ratio phosphatidylcholine to choline is usually more than 0.1, preferably more than 0.26, in particular 0.30-6, more preferably 0.36-3. Herein, the amount of choline in grams is to be calculated as the molar contribution of choline as provided by all choline sources (when orally digested and assuming 100% bioavailability, including PC), times the molecular weight of choline (104 g/mol). Herein, the molecular weight of PC 810 gram/mol. So for example, including 400 mg choline chloride and 200 mg phosphatidylcholine and 200 mg PL's other than PC would then result in a weight ratio of PC to choline of 200/[(104/139.6)×400+(104/810)×200]=200/[298+25.7] =0.62

The presence of PC is in particular preferred as a source for choline, because less PC is required than equimolar choline ingredient (i.e. N,N,N-trimethylethanolammonium cation) for obtaining the same choline concentrations in blood. Herewith choline (salt) content can be reduced, whilst still providing a choline source. Advantageous thereof include avoiding a fishy odour of product and/or subject treated with the product; avoiding irritation of the mucous membranes in case of xerostomia.

The nutritional product usually comprises a protein. The protein content is preferably less than 400 mg per gram dry matter, more, preferably 100-340 mg protein per gram dry matter. A relatively low protein content is preferred to decrease consequences on diet intake. In particular, a relatively low protein content is desired in view of a satiating effect a high protein content has, which may cause the subject to consume an insufficient amount of the nutritional product. For improved palatability and/or for improving brain function. In a liquid product, the protein content preferably is less than 11 g/100 ml, more preferably 5.2-8.2 g/l. In a specific embodiment, the protein content is more than 7 g/100 ml.

In an advantageous embodiment, the nutritional composition comprises at least a whey protein. In a liquid product, the dairy protein content (whey protein, casein, caseinate) preferably is less than 4 wt./vol %.

In an advantageous embodiment, the nutritional composition according to the invention comprises a protein selected from the group of fish proteins (in particular cod protein), egg-protein and vegetable proteins. If present, the total content of non-dairy protein is usually more than 21 wt. % preferably 22-80 wt. %, in particular 25-40 wt. %, based on total protein content. Non-dairy proteins, such as vegetable, fish or egg protein is an advantageous protein source, amongst others because they are less satiating than dairy proteins. Another reason to include such non-dairy protein is an improved endocrine response action, which results in good postprandial glucose response. compared to a dairy protein, in particular compared to casein/caseinate.

A vegetable protein may in particular be selected from the group of potato protein, soy protein, pea protein, beans protein, lupin protein, quinoa protein and amaranth protein.

A composition comprising whey protein and amaranth or pea protein is in particular suitable for increasing BMI. The weight ratio whey protein to the sum of amaranth and pea protein may in particular be 50:50 to 90:10, more in particular 60:40 to 80:20.

A composition comprising whey protein, soy protein and wheat protein is in particular suitable for increasing ADL in subjects suffering from early physical exhaustion after exercise. When present in combination, the whey protein content preferably is 30-70 wt. % of the protein fraction, the pea protein fraction preferably is 15-35 wt. % of the protein fraction, and the soy protein fraction preferably is 15-35 wt. % of the protein fraction. One or more other proteins from other sources may be present in a product comprising proteins from these three protein sources, e.g. casein, usually in a total concentration of up to 40 wt. % of the protein fraction.

The dairy protein or the non-dairy protein may be non-hydrolysed or may be partially hydrolysed. The degree of hydrolysis may in particular be 2-12.

In a specific embodiment, a composition (for use) according to the invention comprises at least one amino source providing L-serine and/or L-aspartic acid. The amino acid source can be selected from free amino acids, including salts thereof, peptides (oligopeptides, polypeptides, proteins), comprising and L-serine unit and/or L-aspartic acid units. If present, the L-serine content preferably is higher than 4.1 g per 100 gram amino acids, including amino acids in peptides and other compounds providing an amino acid when digested. If present, the L-aspartic acid content preferably is 8.4-15 g per 100 gram amino acids including amino acids in peptides and other compounds providing an amino acid when digested.

Preferably, the nutritional composition comprises 0.15-0.5 g digestible carbohydrate per gram dry weight, in particular 0.20-0.40 g digestible carbohydrate per gram dry weight. Preferably, the digestible carbohydrate fraction provides glucose, fructose and galactose (present as monosaccharide or in oligo/polysaccharide form).

Preferably 0.01-0.1 g fibre per g dry weight is present in a composition according to the invention. In particular, the fibre content may be in the range of 0.02-0.08 g per g dry weight.

The lipid content in a nutritional composition according to the invention preferably is 0.15-0.3 g lipids per gram dry weight.

Further, the composition may comprises additional vitamins and/or minerals.

In particular good results have been achieved with a liquid composition according to the invention.

The liquid composition usually has a dry matter content of 15-30 g per 100 ml. The dry matter content preferably is 24 g per 100 ml or less, in order to aid water homeostasis, in particular 16-24 g per 100 ml, more in particular 17-22 g per 100 ml.

The liquid composition preferably has an osmolarity of less than 450 mEq/l, in particular of 120 to 450 mEq/l.

The viscosity of a liquid nutritional composition according to the invention is usually less than 200 mPa·s The liquid composition may in particular be packaged as a unit dose packaging, which may in particular have a liquid composition content in the range of 50-250 ml, more in particular in the range of 100-150 ml.

In a specific embodiment, the composition is a powder, in particular a powder that is reconstitutable with water to provide a liquid product according tot the invention The invention will now be illustrated by the following examples and the experimental part, without being bound or restricted thereto.

EXPERIMENTAL

For Examples 1-4, mice were used that were 3 months old at the start of the experiment. In the test period all mice were considered to be healthy by the Ethical Committee.

Example 1

APP/PS1 mice, were provided with a diet enriched with DHA and UMP (intake per day: DHA=22.8 mg; UMP=23.1 mg) or with a control diet for 3 months The two diets were isocaloric and differed only with respect to DHA and UMP content The amount of fat, carbohydrates and protein was the same between diets. During the 3 months of diet intervention body weight was monitored as was food intake.
Results.

Mice fed the enriched diet showed—on average—a 17.5% increase in body weight after 3 months compared to 14% for the control mice. Food intake was slightly lower in the group which were fed the enriched diet (on average 2.88 gram per day) compared to control mice (on average 3.08 gram per day).
Conclusion.

mice showed an increase in body weight when fed with the composition according to the invention (the ω-3 polyunsaturated fatty acid DHA and the nucleoside UMP), not attributed to a caloric increase in body weight.

Example 2

APP/PS1 mice, were provided with a diet enriched with B-vitamins (B6, B12 and folic acid; intake per day: B6=0.1 mg; B12=0.11 µg; folic acid=18.1 µg), phospholipids (lecithin; intake per day: 12.4 mg) and antioxidants (vitamin C, vitamin E, selenium; intake per day: vitamin C=4.8 mg; vitamin E=4.5 mg; selenium=3.2 µg) or with a control diet for 3 months. The two diets were isocaloric and differed only with respect to B-vitamins, phospholipids and antioxidants content. The amount of fat, carbohydrates and protein was the same between diets. During the 3 months of diet intervention body weight was monitored as was food intake.
Results.

Mice fed the B-vitamins+phospholipids+antioxidants enriched diet showed a 18% increase in body weight after 3 months compared to 14% for the control mice. Food intake was slightly lower in the B-vitamins+phospholipids+antioxidants group (on average 2.86 gram per day) compared to control mice (on average 3.08 gram per day).
Conclusion.

mice showed an increase in body weight when fed with the composition according to the invention (B vitamins, a phospholipid, and antioxidants), not attributed to a caloric increase in body weight.

Example 3

APP/PS1 mice, were provided with a diet enriched with DHA+UMP (intake per day: DHA=22.8 mg; UMP=23.1 mg) (as in Example 1), B-vitamins (B6, B12 and folic acid; intake per day: B6=0.1 mg; B12=0.11 µg; folic acid=18.1 µg), and phospholipids (lecithin; intake per day: 12.4 mg) or with a control diet for 3 months. The two diets were isocaloric and differed only with respect to DHA, UMP, B-vitamins and phospholipids content. The amount of fat, carbohydrates and protein was the same between diets. During the 3 months of diet intervention, body weight was monitored as was food intake.
Results.

Mice fed the enriched diet showed a 20% increase in body weight after 3 months compared to 14% for the control mice. Food intake was the same in the ω-3 PUFA+nucleoside+B-vitamins+phospholipids group (on average 3.02 gram per day) compared to control mice (on average 3.08 gram per day).
Conclusion.

mice showed an increase in body weight when fed with the composition according to the invention (ω-3 polyunsaturated fatty acids, a nucleoside, B vitamins, and phospholipids), not attributed to a caloric increase in body weight.

Example 4

APP/PS1 mice, were provided with a nutritional composition comprising uridine-5'-monophosphate (intake per day: UMP=23.1 mg); omega-3 fatty acids (including DHA) (intake per day: DHA=22.8 mg); choline (intake per day: 12 mg); phospholipids (intake per day: 12.4 mg); B vitamins (intake per day: B6=0.1 mg; 812=0.11 µg; folic acid=18.1 ug), and antioxidants (intake per day: vitamin C=4.8 mg; vitamin E=4.5 mg; selenium=3.2 ug) or with a control diet for 3 months. The two diets were isocaloric. The amount of fat, carbohydrates and protein was the same between diets. During the 3 months of diet intervention, body weight was monitored as was food intake.
Results.

Mice fed the nutritional composition showed a 25% increase in body weight after 3 months compared to 14% for the control mice. Food intake was the same in the group fed the nutritional composition (on average 3.10 gram per day) compared to control mice (on average 3.08 gram per day).
Conclusion.

mice showed an increase in body weight when fed with the composition according to the invention (nucleoside: UMP; ω-3 polyunsaturated fatty acids (including DHA); choline; phospholipids; B vitamins, and antioxidants), not attributed to a caloric increase in body weight.

Example 5

TABLE 1

| Isocaloric drink suitable for increasing BMI | |
|---|---|
| Component | Invention |
| Amount | 125 ml |
| Macronutrients | |
| Energy, kcal | 125 |
| Protein (caseinate/WPI), g | 3.8 |
| Carbohydrate, g | 16.5 |
| Fat, g | 4.9 |
| Components according to invention | |
| eicosapentaenoic acid. mg | 300 |
| docosahexaenoic acid, mg | 1200 |
| Phospholipids, mg | 106 |
| Choline, mg | 400 |
| UMP (uridine monophosphate), mg | 625 |
| Vitamin E (alpha- tocopherol equivalents), mg | 40 |
| Vitamin C, mg | 80 |
| Selenium, µg | 60 |
| Vitamin B12, µg | 3 |
| Vitamin B6, mg | 1 |
| Folic acid, µg | 400 |
| Minerals | |
| Sodium, mg | 125 |
| Potassium, mg | 187.5 |
| Cloride, mg | 156.3 |
| Calcium, mg | 100 |
| Phosphorus, mg | 87.5 |
| Magnesium, mg | 25.0 |
| Other trace elements | |
| Iron, mg | 2 |
| Zinc, mg | 1.5 |
| Iodine, µg | 16.3 |
| Manganese, mg | 0.41 |

TABLE 1-continued

Isocaloric drink suitable for increasing BMI

| Component | Invention |
| --- | --- |
| Copper, µg | 225 |
| Molybdenum, µg | 12.5 |
| Chromium, µg | 8.4 |
| Other vitamins | |
| Vitamin A, µg | 200 |
| Thiamin (B1), mg | 0.19 |
| Riboflavin (B2), mg | 0.20 |
| Niacin (B3), mg niacin equivalent | 2.25 |
| Pantothenic acid (B5), mg | 0.66 |
| Vitamin D, µg | 0.88 |
| Biotin, µg | 5.0 |
| Vitamin K, µg | 6.6 |

TABLE 2

Results of BMI increase (Example 5)

|  | BMI at Baseline | BMI after 3 months | BMI after 6 months |
| --- | --- | --- | --- |
| Invention | 26.198 | 26.469 | 26.58* |
| Control | 26.175 | 26.353 | 26.348 |

*p = 0.088

Example 6

Example Compositions According to the Invention

The following compositions according to the invention may be used for the healthy improvement of body weight in an elderly person, in particular a non-frail or prefrail person experiencing one or two symptoms of frailty, preferably in elderly having a BMI of less than 23.5 kg/m$^2$:

TABLE 3

Composition A (per 100 g of ready-to-use composition)

| | |
| --- | --- |
| Pyrimidine nucleoside | 0.3 g of a mixture of uridine and uridine monophosphate |
| Vitamin B | 1 mg B6, 2 µg B12 and 300 µg folic acid or folate and optionally one or more of: |
| A phospholipid | 0.2 g lecithin |
| A choline | 1 g choline as choline chloride |
| Lipids | 2 g marine or algae oil, comprising 30-60 g of DHA, DPA or EPA per 100 g fatty acids |

TABLE 4

Composition B (sip feed, amount per 100 ml)

| Ingredient | Amount |
| --- | --- |
| Energy | ≥150 kcal (≥ 630 kJ) |
| Protein | ≥3.5 g |
| Digestible carbohydrates | 16 g |
| Fat | 5.2 g |
| DHA | 300 mg |
| EPA | 75 mg |
| Phospholipids | 50 mg |
| UMP | 160 mg |
| Choline | 100 mg |
| Vitamin B6 | 0.3 mg |
| Vitamin B12 | 0.8 µg |
| Folic acid | 100 mg |
| Vitamin C | 20 mg |
| Vitamin E | 10 mg |
| Selenium | 15 µg |
| Vitamin D | 1.2 µg |
| Calcium | 200 mg |

TABLE 5

Composition C to F

| Components | Composition C | Composition D | Composition E | Composition F |
| --- | --- | --- | --- | --- |
| Macronutrients | | | | |
| Energy (kcal) | 140 | 100 | 150 | 140 |
| Protein (g) | 8 (milk protein + blend soy prot/α-lac) | 3 (milk protein) | 10 (ultra filtrated milk protein + free leucine) | 8 (pea protein, casein, a-lac) |
| Lipids (EPA, DHA, phospholipids) (g) | 5.8 | 3.9 | 5.1 | 5.1 |
| Digestible carbohydrates (g) | 14 | 13.2 | 16 | 14 |
| Fiber (g) | 0.2 | 0 | 0.2 | 0 |
| EPA (mg) | 120 | 240 | 240 | 200 |
| DHA (mg) | 480 | 960 | 960 | 800 |
| Phospholipids (mg) | 210 | 128 | 128 | 160 |
| Choline (mg) | 200-300 | 320 | 320 | 260 |
| UMP (mg) | 250 | 500 | 500 | 400 |
| Vitamin E (mg α-TE) | 16 | 32 | 32 | 25 |
| Vitamin C (mg) | 32 | 64 | 64 | 50 |
| Selenium (µg) | 67 | 48 | 48 | 50 |
| Vitamin B12 (µg) | 2.4 | 2.4 | 2.4 | 2 |
| Vitamin B6 (mg) | 0.8 | 0.8 | 0.8 | 1 |
| Folates (µg) | 320 | 320 | 320 | 280 |
| Sodium (mg) | 100 | 100 | 100 | 100 |
| Potassium (mg) | 100-200 | 150 | 100-200 | 100-200 |
| Chloride (mg) | 100-150 | 125 | 100-150 | 100-150 |
| Calcium (mg) | 100-300 | 80 | 100-300 | 100-300 |
| Phosphorus (mg) | 100-300 | 70 | 100-300 | 100-300 |
| Magnesium (mg) | 32 | 23.2 | 23.2 | 23.2 |
| Iron (mg) | 1.6 | 1.6 | 1.6 | 1.4 |
| Zinc (mg) | 2.4 | 1.2 | 1.2 | 2 |
| Iodine (µg) | 26 | 13 | 13 | 20 |
| Manganese (mg) | 0.88 | 0.33 | 0.33 | 0.4 |
| Copper (µg) | 180 | 180 | 180 | 150 |
| Molybdenum (µg) | 26 | 10 | 10 | 20 |
| Chromium (µg) | 6.7 | 6.7 | 6.7 | 8 |
| Vitamin A (µg) | 160 | 160 | 160 | 140 |
| Thiamine (mg) | 0.21 | 0.15 | 0.15 | 0.16 |
| Riboflavin (mg) | 0.23 | 0.16 | 0.16 | 0.18 |
| Niacin (mg) | 2.5 | 1.8 | 1.8 | 2 |
| Patothenic acid (mg) | 1.4 | 0.53 | 0.53 | 0.6 |
| Vitamin D (µg) | 4-7 | 0.7 | 0.7 | 2 |
| Biotin (µg) | 10.5 | 4.0 | 4 | 6 |
| Vitamin K (µg) | 14 | 5.3 | 5.3 | 6 |

TABLE 6

Composition G: Product comprising per 1000 litres (about)

| Ingredient | Amount (kg) |
| --- | --- |
| Ultrafiltrated dairy protein | 700 |
| Superrefined Tuna Fish Oil | 18 |
| Lecithin Powder | 0.9 |
| Sugar | 42 |
| Maltodextrin | 118 |

TABLE 6-continued

Composition G: Product comprising per 1000 litres (about)

| Ingredient | Amount (kg) |
|---|---|
| Rapeseed-Sunflower-High Oleic Blend | 32 |
| Choline chloride | 2 |
| UMP | 3.7 |
| Potassium hydroxide | 0.27 |
| Citric Acid Monohydraat | 1.3 |
| Magnesium hydroxide | 0.6 |
| Tri-potassium citrate.1aq | 0.9 |
| Mineral Premix | 0.2 |
| Vitamin Premix | 1.0 |
| Vanilla Flavour | 1.2 |
| Water | added to 1000 l |

Example 7

Tool for Assessing the Degree of Frailty of a Subject

Consists of answering a fixed set of questions, each related to one or more of the aspects of frailty, and scoring the replies by comparison with normal values.

In order to correctly answer the questions, specific measurements are recommended, as described in the text.

The questions can be asked by an expert and orally replied to; alternatively they can also be put on a paper or form and the replies written down; however, preferably the questions can be raised on a screen or monitor of an electronic device, like a small computer, tablet or peripheral station of a central computer system.

The electronic device can have the normal values stored and can be equipped with software which allows automatic calculation of scores per parameter and of the frailty index.

The algorithm to calculate the final score can be subject to individual medical expertise. However, it is preferred to operate with a common algorithm to allow comparison of diagnosis. In the text of the document, it is described how this can occur. It is preferred to score the value of each individual parameter by comparison with age-matched controls; when the subject scores positive on two of the parameters as given below the subject is defined to be prefrail and can be helped by the composition according to the invention according the invention. When the subject scores positive on at least three parameters, the individual is diagnosed to be frail and to be receptive for improvement by use of the composition according to the invention.

TABLE 7

Example of a questionnaire for scoring frailty.

| Parameter | Measurements | Normal value/Score |
|---|---|---|
| Muscle weakness | Muscle: method: Value | |
| Excessive feelings of exhaustion or fatigue | Mental fatigue Perceived fatigue after exercise: Activities of daily living (ADL)/sleep needed Muscle capacity or power Speed of developing fatigue Lung capacity | |
| Abnormally low physical activity | Voluntary normal activities Capabilities to apply instrumental activities | |
| Slow or unsteady gait | One or more or combinations of balance, effort (walking time) and coordination | |

TABLE 7-continued

Example of a questionnaire for scoring frailty.

| Parameter | Measurements | Normal value/Score |
|---|---|---|
| Weight loss | Average involuntary weight loss (BMI, LBM) Absence of acute weight loss or an acute phase response | |
| Neurological dysfunction | Cognitive impairment Memory disorder Sensory impairment Motoric impairment Chronic pain Depression Sleep disorder Anxiety disorder | |
| TOTAL SCORE | Prefrail: 2 Mildly frail: 3 Moderately frail: 4 Severely frail: 5-6 | |

Example 8

Further Formulation Examples

TABLE 8

Ready to feed liquid formulations

| Component | Composition $H^1$ | Composition $I^2$ | Composition $J^3$ |
|---|---|---|---|
| Volume per packaging | 125 ml | 125 ml | 125 m; |
| Energy density (kcal/ml) | 1.0 | 1.6 | 1.6 |
| Protein (g/100 ml) Ingredients/ components | 7.5 (i) Whey and (ii) amaranth or pea protein (70:30) | 10 Whey protein | 8 Whey protein, soy protein pea protein and casein (35:20:20:25 |
| Lipids (g/100 ml) Ingredients/ components | 5.1 Phospholipids = 220 mg Fish oil/rape seed/ lecithin 10:7:1 by wt, providing 600 mg DHA and 150 mg EPA | 8 PL's 400 mg Marine oil/corn oil/palm oil/lecithin to result in 600 mg and 150 mg EPA | 8 Lecithin 420 mg Marine oil/soy/ canola/lecithin to get 600 mg DHA and 150 mg EPA |
| Digestible Carbohydrates (g/100 ml) | 6 after hydrolyses of ingredients by weight: 10% galactose, 60% glucose, 10% fructose, and 10% other monosaccharides | 9.5 | 11.5 |
| Fiber (g/100 ml) | 1.5 Inuline hydrolysate + galacto-OS and manno OS (60:20:20 by wt) | 1.5 Inuline hydrolysate + galacto-OS and manno OS (60:20:20 by wt) | 1.5 Inuline hydrolysate + galacto-OS and manno OS (60:20:20 by wt) |
| Choline (mg/100 ml) | 200 Choline alfosclerate | 200 Choline alfosclerate | 200 Choline alfosclerate |
| Uridine source (mg/100 ml) | 310 Uridine + UMP 4:6 by wt | 320 Uridine + UMP 2:8 by weight | 310 Uridine + UMP 3:7 by weight |

TABLE 8-continued

Ready to feed liquid formulations

| Component | Composition H[1] | Composition I[2] | Composition J[3] |
|---|---|---|---|
| Vitamins (amounts per 100 ml) | Folates: 200 ug<br>B12: 6 ug<br>B6: 1 mg<br>Vitamin E: 20 mg<br>Vitamin C: 40 mg<br>Vitamin premix providing all vitamins except the above in 0.2xRDA of FDA 1988 | Folates: 200 ug<br>B12: 6 ug<br>B6: 1 mg<br>Vitamin E: 20 mg<br>Vitamin C: 40 mg<br>Vitamin premix providing all vitamins except the above in 0.2xRDA of FDA 1988 | Folates: 200 ug<br>B12: 6 ug<br>B6: 1 mg<br>Vitamin E: 20 mg<br>Vitamin C: 40 mg<br>Vitamin premix providing all vitamins except the above in 0.2xRDA of FDA 1988 |
| Minerals (amounts/ml) | Se: 30 ug<br>Fe: 2 mg<br>Zn: 1.5 mg<br>Mg: 25 mg<br>Ca: 120 mg<br>Na: 120 mg<br>K: 180 mg<br>Cl: 150 mg<br>P: 90 mg<br>I: 16 ug<br>Mn: 0.5 mg<br>Cu: 0.23 mg<br>Mo: 13 ug<br>Cr: 8 ug | Se: 30 ug<br>Fe: 2 mg<br>Zn: 1.5 mg<br>Mg: 25 mg<br>Ca: 120 mg<br>Na: 120 mg<br>K: 180 mg<br>Cl: 150 mg<br>P: 90 mg<br>I: 16 ug<br>Mn: 0.5 mg<br>Cu: 0.23 mg<br>Mo: 13 ug<br>Cr: 8 ug | Se: 30 ug<br>Fe: 2 mg<br>Zn: 1.5 mg<br>Mg: 25 mg<br>Ca: 120 mg<br>Na: 120 mg<br>K: 180 mg<br>Cl: 150 mg<br>P: 90 mg<br>I: 16 ug<br>Mn: 0.5 mg<br>Cu: 0.23 mg<br>Mo: 13 ug<br>Cr: 8 ug |

[1]Product in particular suitable for increasing body mass index
[2]Product in particular suitable for increasing lean body mass (LBM) in non-frail elderly
[3]Product in particular suitable for increasing ADL in persons suffering from early physical exhaustion after exercise Example 9

Improving BMI

Mice, 3 months of age, were provided with a diet (AIN-93) enriched with a combination of DHA+UMP (intake per day: DHA=22.8 mg; UMP=23.1 mg), B-vitamins (B6, B12 and folic acid; intake per day: B6=0.1 mg; B12=0.11 ug; folic acid=18.1 ug), and phospholipids (lecithin; intake per day: 12.4 mg) or with a control diet (AIN-93) for 3 months. The two diets were isocaloric and differed only with respect to DHA, UMP, B-vitamins and phospholipids content. The amount of fat, carbohydrates and protein was the same between diets. During the 3 months of diet intervention bodyweight was monitored as was food intake.

Results

Mice fed the enriched diet showed a 17.8% increase in bodyweight after 3 months compared to 11.5% for the control mice. Food intake was the same in the n3PUFA+nucleotide+B-vitamins+phospholipids group (on average 3.02 gram per day) compared to control mice (on average 3.08 gram per day).

Conclusion n3PUFA+nucleotide+B-vitamins+phospholipids increases bodyweight without an increase in caloric intake.

Example 10

Improving BMI

Mice, 3 months of age, were provided with a diet (AIN-93) enriched with a combination of uridine-5'-monophosphate (intake per day: UMP=23.1 mg); omega-3 fatty acids (including DHA) (intake per day: DHA=22.8 mg); choline (intake per day: 12 mg); phospholipids (lecithin; intake per day: 12.4 mg); B vitamins (B6, B12 and folic acid; intake per day: B6=0.1 mg; B12=0.11 ug; folic acid=18.1 ug), and antioxidants (intake per day: vitamin C=4.8 mg; vitamin E=4.5 mg; selenium=3.2 ug) or with a control diet (AIN-93) for 3 months. The two diets were isocaloric. The amount of fat, carbohydrates and protein was the same between diets. During the 3 months of diet intervention bodyweight was monitored as was food intake.

Results

Mice fed the enriched diet showed a 22% increase in bodyweight after 3 months compared to 11.5% for the control mice. Food intake was the same in the enriched diet group (on average 3.10 gram per day) compared to control mice (on average 3.08 gram per day).

Conclusion

The combination of uridine-5'-monophosphate; omega-3 fatty acids (including DHA); choline; phospholipids; B vitamins, and antioxidants increases bodyweight without an increase in caloric intake.

Example 11

Tablet comprising 500 mg uridinemonophosphate, uridine or citicoline (cytidine diphosphate-choline), combined with 300 microgram sodium folate monglutamate and 5 microgram vitamin B12 and conventional tabletting aids, like binders, inert filling aids, colorants, etc., to provide a tablet of about 1 g.

The tablet is in particular suitable for increasing BMI in an elderly person. The skilled person will be able to provide a different dosage form providing the same or similar active ingredients in the same or other suitable dosage, based on the information disclosed herein and common general knowledge.

Example 12

Tablet comprising 400 mg of a nucleoside equivalent, like uridine, 6 mg vitamin B6, 200 micrrogram folate, 5 microgram vitaminB12 and 400 mg of a choline equivalent included in conventional tabletting aids to provide a tablet of about 1 g.

The tablet is in particular suitable for increasing BMI in an elderly person. The skilled person will be able to provide a different dosage form providing the same or similar active ingredients in the same or other suitable dosage, based on the information disclosed herein and common general knowledge.

Example 13

Capsule weighing about 1.9 g, comprising 700 mg marine oil, 300 mg soy lecithin, 100 mg of uridine, 100 mg of UMP, 100 microgram of folate, 5 mg vitamin B6, 20 microgram vitamin B12, 10 mg vitamin E (as alpha-tocopherol) and 20 mg vitamin C, the remainder being capsulating material, e.g. gelatin, The capsule is in particular suitable for increasing BMI in an elderly person. The skilled person will be able to provide a different dosage form providing the same or similar active ingredients in the same or other suitable dosage, based on the information disclosed herein and common general knowledge.

The invention claimed is:

1. A method of increasing or maintaining body weight of a human comprising selecting a human with involuntary weight loss and assessing nutritional status of the human and administering to the human a composition including at least two components selected from the group consisting of (i) a nucleoside equivalent, (ii) an n-3 polyunsaturated fatty acid selected from the group consisting of DHA, DPA and EPA, (iii) a vitamin B selected from the group consisting of vitamin B6, vitamin B9 and vitamin B12 (iv) a phospholipid, (v) an antioxidant selected from the group consisting of vitamin C, vitamin E and selenium, and (vi) a choline in a manner to increase or maintain body weight of the human, with the proviso that at least one nucleoside equivalent or at least one vitamin B is present, wherein the composition is administered to the human in a diet without essentially increasing the daily caloric intake of the human.

2. The method of claim 1, wherein the increase or maintenance in body weight comprises one or more of (i) increasing or maintaining lean body weight and (ii) increasing or maintaining muscle mass.

3. The method of claim 1, wherein body mass index is increased or maintained.

4. A method for improving the ability to perform an activity of daily living of a human with involuntary weight loss, for maintaining the ability to perform an activity of daily living of a human with involuntary weight loss, or for reducing a deterioration in the ability to perform an activity of daily living of a human with involuntary weight loss comprising selecting a human with involuntary weight loss and assessing nutritional status of the human and administering to the human a composition including at least two components selected from the group consisting of (i) a nucleoside equivalent, (ii) an n-3 polyunsaturated fatty acid selected from the group consisting of DHA, DPA and EPA, (iii) a vitamin B selected from the group consisting of vitamin B6, vitamin B9 and vitamin B12 (iv) a phospholipid, (v) an antioxidant selected from the group consisting of vitamin C, vitamin E and selenium and (vi) a choline in a manner to improve the ability to perform an activity of daily living of the human, to maintain the ability to perform an activity of daily living of the human, or to reduce a deterioration in the ability to perform an activity of daily living of the human, wherein the composition is administered to the human in a diet without essentially increasing the daily caloric intake of the human and wherein the body weight of the human is maintained or increased.

5. The method of claim 4, wherein the human has a PASE-value score of 55 or less.

6. The method of claim 1, wherein the composition includes at least three components selected from the group consisting of (i) a nucleoside equivalent, (ii) an n-3 polyunsaturated fatty acid selected from the group consisting of DHA, DPA and EPA, (iii) a vitamin B, (iv) a phospholipid, (v) an antioxidant and (vi) a choline.

7. The method of claim 1, wherein the composition includes at least four components selected from the group consisting of (i) a nucleoside equivalent, (ii) a n-3 polyunsaturated fatty acid selected from the group consisting of DHA, DPA and EPA, (iii) a vitamin B, (iv) a phospholipid, (v) an antioxidant and (vi) a choline.

8. The method of claim 1, wherein the human is non-frail and/or does not have dementia.

9. The method of claim 1, wherein the human is an elderly human.

10. The method of claim 1, wherein the human, who when starting with the use, has had a weight loss of 2-4.5 kg in the year preceding the start or 4-6 kg in the two years preceding the start.

11. The method of claim 1, wherein the nucleoside equivalent comprises a uridine source.

12. The method of claim 1, wherein the phospholipid is selected from the group consisting of phosphatidylserine, phosphatidylinositol, phosphatidylcholine and phosphatidylethanolamine.

13. The method of claim 1, wherein the composition is administered to the human as part of a nutritional composition.

14. Nutritional composition, comprising
  i-) uridine and/or uridine monophosphate
  ii) DHA and EPA
  iii) a vitamin B selected from the group consisting of vitamin B6, vitamin B9 and vitamin B12
  iv) a phospholipid
  v) an antioxidant selected from the group consisting of vitamin C, vitamin E and selenium
  vi) a choline
  vii) a protein,
  wherein the composition comprises phosphatidylcholine, and the weight to weight ratio phosphatidylcholine to choline is more than 0.26.

15. Nutritional composition according to claim 14, wherein the weight to weight ratio urdine to uridine monophosphate is in the range of 0.2:1 to 0.7:1.

16. Nutritional composition according to claim 14, wherein the total content of uridine plus uridine monophosphate is in the range of 5-30 mg per gram dry weight.

17. Nutritional composition according to claim 14, comprising 5-10 mg EPA per gram dry weight and 2.5-20 mg DHA per gram dry weight.

18. Nutritional composition according to claim 14, wherein, the protein content is less than 400 mg per gram dry matter.

19. Nutritional composition according to claim 14, having an energy density of less than 13 kcal per gram dry matter.

20. Nutritional composition according to claim 14, wherein the phospholipid content is in the range of 3.3-67 mg/gram dry matter.

21. Nutritional composition according to claim 14, wherein the weight ratio phosphatidylcholine to choline is 0.26-6.

22. Nutritional composition according to claim 14, wherein the composition comprises (iii) vitamin B6, vitamin B12 and vitamin B9, (v) vitamin C, vitamin E and selenium and (vi) at least one choline selected from the group consisting of choline chloride and choline alfosclerate.

23. Nutritional composition according to claim 14, wherein the composition comprises at least two different phospholipids selected from the group consisting of phosphatidylserine, phosphatidylinositol, phosphatidylcholine and phosphatidylethanolamine.

24. Nutritional composition according to claim 14, wherein the ratio [uridine monophosphate+uridine]/[phospholipds] is less than 5.9.

25. Nutritional composition according to claim 14, wherein the nutritional composition comprises at least a whey protein.

26. Nutritional composition according to claim 14, comprising a protein selected from the group consisting of fish proteins, egg-protein and vegetable proteins.

27. Nutritional composition according to claim 26, comprising a vegetable protein selected from the group consisting of potato protein, soy protein, pea protein, beans protein, lupin protein, quinoa protein and amaranth protein.

28. Nutritional composition according to claim 14, comprising one or more proteins, wherein the total content of non-dairy protein is more than 21 wt. %.

29. Nutritional composition according to claim 14, comprising 0.15-0.5 g digestible carbohydrate per gram dry weight.

30. Nutritional composition according to claim 14, comprising 0.15-0.3 g lipids per gram dry weight.

31. Nutritional composition according to claim 14, wherein the composition is a liquid.

32. Nutritional composition according to claim 31, having a dry matter content of 15-30 g per 100 ml.

33. Nutritional composition according to claim 31 having an osmolarity of less than 450 mEq/l.

34. Nutritional composition according to claim 14, wherein the composition is a powder.

\* \* \* \* \*